US012629387B2

(12) United States Patent
Tai et al.

(10) Patent No.: US 12,629,387 B2
(45) Date of Patent: May 19, 2026

(54) COMPOSITION OF ANTIVIRAL AGENT FOR USE IN PROPHYLACTIC OR POST-EXPOSURE TREATMENT OF INFECTIOUS OR RESPIRATORY DISEASES

(71) Applicant: InspirMed Corp., Taipei City (TW)

(72) Inventors: Tien-Tzu Tai, Taipei (TW); Yun-Long Tseng, Taipei (TW); Ting-Yu Cheng, Taipei (TW); Sheue-Fang Shih, Taipei (TW); He-Ru Chen, Taipei (TW); Keelung Hong, South San Francisco, CA (US); Jonathan Fang, South San Francisco, CA (US)

(73) Assignee: INSPIRMED CORP., Taipei City (TW)

( * ) Notice: Subject to any disclaimer, the term of this patent is extended or adjusted under 35 U.S.C. 154(b) by 773 days.

(21) Appl. No.: 17/912,933

(22) PCT Filed: Mar. 22, 2021

(86) PCT No.: PCT/US2021/023405

§ 371 (c)(1),
(2) Date: Sep. 20, 2022

(87) PCT Pub. No.: WO2021/194927

PCT Pub. Date: Sep. 30, 2021

(65) Prior Publication Data

US 2023/0181615 A1 Jun. 15, 2023

Related U.S. Application Data

(60) Provisional application No. 63/134,645, filed on Jan. 7, 2021, provisional application No. 63/017,297, filed on Apr. 29, 2020, provisional application No. 62/993,060, filed on Mar. 22, 2020.

(51) Int. Cl.

| | |
|---|---|
| ***A61K 31/7076*** | (2006.01) |
| ***A61K 9/127*** | (2006.01) |
| ***A61K 47/28*** | (2006.01) |
| ***A61K 47/69*** | (2017.01) |
| ***A61P 31/12*** | (2006.01) |

(52) U.S. Cl.

CPC .......... *A61K 31/7076* (2013.01); *A61K 9/127* (2013.01); *A61K 47/28* (2013.01); *A61K 47/6911* (2017.08); *A61P 31/12* (2018.01)

(58) Field of Classification Search

None

See application file for complete search history.

(56) References Cited

U.S. PATENT DOCUMENTS

| | | | | |
|---|---|---|---|---|
| 7,964,580 | B2 | 6/2011 | Sofia et al. | |
| 8,008,264 | B2 | 8/2011 | Butler et al. | |
| 8,415,308 | B2 * | 4/2013 | Cho | C07F 9/00 514/23 |
| 9,481,704 | B2 | 11/2016 | Clarke | |
| 2007/0196461 | A1 | 8/2007 | Weers | |
| 2008/0138397 | A1 | 6/2008 | Schuster et al. | |
| 2011/0104259 | A1 | 5/2011 | Schuster et al. | |
| 2019/0350853 | A1 | 11/2019 | Ho et al. | |

FOREIGN PATENT DOCUMENTS

| | | | |
|---|---|---|---|
| CN | 111991375 | A | 11/2020 |
| CN | 111991401 | A | 11/2020 |
| CN | 114292272 | A | 4/2022 |
| EP | 0267050 | A2 | 11/1988 |
| WO | 2005/020885 | A2 | 3/2005 |
| WO | 2005107712 | A1 | 11/2005 |
| WO | 2007067520 | A2 | 6/2007 |
| WO | 2009132135 | A1 | 10/2009 |
| WO | 2013138236 | A1 | 9/2013 |
| WO | 2017184668 | A1 | 10/2017 |
| WO | 2019209787 | A1 | 10/2019 |

OTHER PUBLICATIONS

Desu, Hari R. "Targeted delivery of surface modified nanoparticles: modulation of inflammation for acute lung injury." (2009).*

Rajendran, Vinoth, et al. "Therapeutic Efficacy of Chloroquine in Long Circulating Liposome Formulations Against Chloroquine-Resistant Plasmodium Berghei Infection in Mice." European Journal of Biomedical 3.11 (2016): 258-264.*

Plantone, Domenico, and Tatiana Koudriavtseva. "Current and future use of chloroquine and hydroxychloroquine in infectious, immune, neoplastic, and neurological diseases: a mini-review." Clinical drug investigation 38 (2018): 653-671.*

Allen, Theresa M., and Pieter R. Cullis. "Liposomal drug delivery systems: from concept to clinical applications." Advanced drug delivery reviews 65.1 (2013): 36-48.*

DASH and Badireenath Konkimalla. "Selection of P-Glycoprotein Inhibitor and Formulation of Combinational Nanoformulation Containing Selected Agent Curcumin and DOX for Reversal of Resistance in K562 Cells", Pharm Res Aug. 2017; 34(8): 1741-1750. [10 pages].

Kende et al. "Enhanced Efficacy of Liposome-Encapsulated Ribavarin Against Rift Valley Fever Virus Infection in Mice", Antimicrob. Agents Chemother. 27: 903-907 (Jun. 1985). [5 pages].

Liu et al. "Hydroxychloroquine, a less toxic derivative of chloroquine, is effective at inhibiting SARS-CoV-2 infection in vitro", Cell Discovery (2020) 6:16. [4 pages].

Humeniuk et al. "Safety, Tolerability, and Pharmacokinetics of Remdesivir, An Antiviral for Treatment of COVID-19, in Healthy Subjects", Clin Transl Sci. 2020; 13(5):896-906. [11 pages].

(Continued)

*Primary Examiner* — Patrick T Lewis

(74) *Attorney, Agent, or Firm* — LEASON ELLIS LLP

(57) ABSTRACT

Provided is a composition of antiviral agent for use in prophylaxis or treatment against pathogenic infection. The liposomal antiviral agent of the composition has a liposome and an antiviral agent entrapped in the liposome. The antiviral agent has been stably encapsulated in the liposome, and the resulting liposomal antiviral agent is proven to be stably aerosolized or nebulized for administration via the inhalation route to treat a subject in need thereof with reduced side effect.

23 Claims, 5 Drawing Sheets

(56) References Cited

OTHER PUBLICATIONS

Rouser et al. "Two dimensional thin layer chromatographic separation of polar lipids and determination of phospholipids by phosphorus analysis of spots", Lipids; May 1970, 5, 494-496. [3 pages].
Tai et al., A Strategy to Treat COVID-19 Disease With Targeted Delivery of Inhalable Liposomal Hydroxychloroquine: A Preclinical Pharmacokinetic Study, Clin Transl Sci., 2021, vol. 14, 132-136.
Gilbert et al., Pulmonary delivery of antiviral drugs in liposome aerosols, Seminars in Pediatric Infectious Diseases, 1996, vol. 7, Issue 2, 148-154.
Knight et al., Antiviral therapy with small particle aerosols, Eur J Clin Microbiol Infect Dis., 1988, 7(6), 721-731.
Wong et al., Liposome-mediated immunotherapy against respiratory influenza virus infection using double-stranded RNA poly ICLC, Vaccine, 1999, 17(13-14), 1788-1795.
International Search Report and Written Opinion of PCT/US2021/023405, mailed Jul. 6, 2021.
Murphy et al. "The nucleoside analog GS-441524 strongly inhibits feline infectious peritonitis (FIP) virus in tissue culture and experimental cat infection studies" Veterinary Microbology, vol. 291, 2018, pp. 226-233.

* cited by examiner

COMPOSITION OF ANTIVIRAL AGENT FOR USE IN PROPHYLACTIC OR POST-EXPOSURE TREATMENT OF INFECTIOUS OR RESPIRATORY DISEASES

BACKGROUND

Technical Field

The present invention relates to a drug delivery system for delivery of an antiviral agent. The present invention relates to a method of preparing the drug delivery system. The present invention also relates to a sustained-release pharmaceutical composition adapted to pulmonary delivery system, which has a reduced systemic side effect.

Description of Related Art

Infectious disease could be transmitted by different route of infection such as contact, droplet, and blood-borne infection and bioavailability of drug at affected physical environment could be low by systematic administration of the drug. The penetration of drug delivery system onto target cells of the target tissues is the critical obstacle to effectively treating infectious diseases, such as lung infectious diseases via inhalation. Whilst drug substance retention inside liposome before drug delivery system attachment to the target epithelial cell can alter from one liposomal drug to another liposomal drug based on diffusion rate of free, uncharged drug substance across the lipid membrane of the liposomes, which highly depends on physicochemical properties of the lipid barriers in the presence of microenvironment outside the liposomes, as well as the aqueous environment inside the same.

Respiratory disease caused by infection or other unknown reason is an extremely serious, debilitating lung disease that leads to early death among all, especially those that are characterized by ensuing efficient viral replication and cell damage caused by virus-induced cytolysis or immunopathology. Infected cell lines and postmortem lung tissues have shown cytopathic changes due to apoptosis, necrosis, or occasionally syncytium formation.

Liposomes have been utilized as drug carriers for masking unpleasant taste of drug via inhalation in the treatment of asthma as described in the U.S. Patent Publication No. US20110104259A1. Liposome encapsulation of drug substance could alter the pharmacokinetic profile of the drug substance, provide slow drug release at a local physical environment, allow for optimal administered doses with less frequent drug administration, and/or possibly reduces side effects and toxicity. However, it is not known via inhalation route whether quinine compound or other antiviral agents delivered by the liposome as whole would effectively exert required functions, such as deposition onto the target cell lines expressing suitable receptors as docket site for the virus's entrance to intracellular target sites and perform a desired pharmacokinetic profile in vivo.

It is not readily apparent that utilizing liposome technology to reformulate antiviral agents can yield a liposomal formulation for inhalation at a prophylactic dose to prevent severe acute respiratory syndrome or a therapeutic dose to treat respiratory diseases or infectious diseases with a reduced side effect. Currently, there have been no practicable liposomal drug formulations for inhalation as drug products for chemoprophylaxis as prevention, treatment of mild cases, treatment of acute respiratory distress syndrome (ARDS), acute lung injury (ALI) or severe acute respiratory syndrome (SARS) caused by infection of virus, such as coronavirus, COVID-19, also known as SARS-CoV2.

There remains an unmet need for an inhalable formulation with a predetermined encapsulation efficiency to achieve a balance by reducing dosing frequency and/or dosage for antiviral agents, such as quinine compounds and nucleoside compounds, and targeting a desired prophylactic or therapeutic window for pulmonary delivery. In addition, the formulation suitable for respiratory diseases should have the following properties: being inhalable, showing enough encapsulation efficiency after nebulization, having an improved stability or proper resistance to destruction by local substances, such as lung surfactant, and furthermore, having desired dose strength to ensure the potential for reaching the desired efficacy in the pulmonary environment. The present invention addresses this need and other needs.

SUMMARY

The present invention provides a liposomal drug formulation for treatment of respiratory diseases or infectious diseases, particularly via inhalation, which comprises at least one lipid optionally phospholipid(s) and a sterol, and/or polyethylene glycol (PEG)-modified phospholipid; and an antiviral agent encapsulated in the aqueous interior of the liposome.

To improve upon existing treatment paradigms of respiratory diseases or infectious diseases, and take advantage of the benefits of slow, sustained drug release, we developed a composition of antiviral agent comprising liposomal antiviral agent and a predetermined amount of free antiviral agent in an aqueous suspension that can be aerosolized and inhaled for prophylactic or enhanced treatment of respiratory disease. Particularly, there is a need for inhalable formulations for SARS prophylaxis or treatment.

The present disclosure provides a composition of antiviral agent for use in prophylaxis or treatment of a respiratory disease or an infectious disease, particularly to SARS, having the advantages of: 1) achieving a longer therapeutic effect compared to inhaled free drug substance, 2) delivering the drug directly to the disease site or virus infected site, 3) quicker onset of action, 4) reducing adverse drug reactions and systemic effects, 5) bypassing first-pass metabolism observed in oral dosing, thus increasing the bioavailability of the drug substance (and possibly reducing cardiotoxicity, ocular symptoms of retinopathy, gastrointestinal (GI) effects, including nausea, vomiting, diarrhea and abdominal discomfort and hepatotoxicity), 6) increasing the residence time of the drug substance in target tissue via sustained release from liposomal drug, 7) decreasing the frequency of drug administration, 8) non-invasive inhalation delivery, and/or 9) improving patient outcomes and compliance.

In a particular embodiment, the antiviral agent according to the present disclosure is encapsulated in the liposome at a determined amount to form a composition of antiviral agent according to the present disclosure in order to achieve the composition with a preferred release profile and reduced toxicity, particularly to cardiotoxicity.

Provided is a composition of antiviral agent for use in treatment or prophylaxis of respiratory disease, which is inhalable and comprises liposomal antiviral agent, wherein the liposomal antiviral agent comprises:

a liposome comprising:

- at least one lipid; and
- an antiviral agent encapsulated in the liposome.

In some embodiments, the liposome comprises a lipid bilayer composed of one or more phospholipids and a sterol, wherein the sterol is cholesterol, and phospholipid(s):cholesterol is at a molar ratio from 1:1 to 2:1, optionally 3:2.

In some embodiments, the one or more phospholipids includes phosphocholine (PC), which can, but not be limited to hydrogenated soy phosphatidylcholine (HSPC), 1,2-distearoyl-sn-glycero-3-phosphocholine (DSPC), 1,2-dipalmitoyl-sn-glycero-3-phosphocholine (DPPC), or a mixture thereof. In some other embodiments, the one or more phospholipids comprises DSPC and 1,2-dipalmitoyl-sn-glycero-3-phosphoethanolamine (DPPE) at a molar ratio of 1:1 or 3:2.

In some embodiments, the liposomal antiviral agent comprises 4-aminoquinoline compound.

In some embodiments, the 4-aminoquinoline compound is selected from the group consisting of chloroquine, and hydroxychloroquine and amodiaquine.

In some embodiments, the antiviral agent comprises a nucleoside compound of structural formula I, (I)

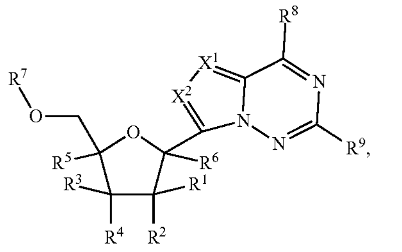

each $R^1$, $R^2$ $R^3$, $R^4$ or $R^5$ is independently H, $OR^a$, $N(R^a)_2$, $N_3$, CN, $NO_2$, $S(O)_nR^a$, halogen or methyl, wherein n is 0, 1 or 2;

$R^6$ is CN or H;

each $R^a$ is independently H, $(C_1\text{-}C_8)$alkyl, $(C_2\text{-}C_8)$alkenyl, $(C_2\text{-}C_8)$alkynyl, aryl$(C_1\text{-}C_8)$alkyl, $(C_4\text{-}C_8)$carbocyclylalkyl, $—C(=O)R^{11}$, $—C(=O)OR^{11}$, $—C(=O)NR^{11}R^{12}$, $—C(=O)SR^{11}$, $—S(O)R^{11}$, $—S(O)_2R^{11}$, $—S(O)(OR^{11})$, $—S(O)_2(OR^{11})$, or $—SO_2NR^{11}R^{12}$; and $R^7$ is H;

Each $X^1$ or $X^2$ is independently $C—R^{10}$ or N;

$R^8$ is halogen, $NR^{11}R^{12}$, $N(R^{11})(OR^{11})$, $NR^{11}NR^{11}R^{12}$, $N_3$, NO, $NO_2$, CHO, CN, $—CH(=NR^{11})$, $—CH=NHNR^{11}$, $—CH=N(OR^{11})$, $—CH(OR^{11})_2$, $—C(=O)NR^{11}R^{12}$, $—C(=S)NR^{11}R^{12}$, $—C(=O)OR^{11}$, $(C_1\text{-}C_8)$alkyl, $(C_2\text{-}C_8)$alkenyl, $(C_2\text{-}C_8)$alkynyl, aryl$(C_1\text{-}C_8)$alkyl, $(C_4\text{-}C_8)$carbocyclylalkyl, optionally substituted aryl, optionally substituted heteroaryl, $—C(=O)(C_1\text{-}C_8)$alkyl, $—S(O)_n(C_1\text{-}C_8)$alkyl, aryl$(C_1\text{-}C_8)$alkyl, $OR^{11}$ or $SR^{11}$;

wherein each aryl or heteroaryl is independently optionally substituted with one or more Z groups;

each $R^9$ or $R^{10}$ is independently H, halogen, $R^{11}$, $OR^{11}$, $SR^{11}$, $NR^{11}R^{12}$, $N(R^{11})(OR^{11})$, $NR^{11}NR^{11}R^{12}$, $N_3$, NO, $NO_2$, CHO, CN, $—CH(=NR^{11})$, $—CH=NHNR^{11}$, $—CH=N(OR^{11})$, $—CH(OR^{11})_2$, $—C(=O)NR^{11}R^{12}$, $—C(=S)NR^{11}R^{12}$, $—C(=O)OR^{11}$;

each $R^{11}$ or $R^{12}$ is independently H, $(C_1\text{-}C_8)$alkyl, $(C_2\text{-}C_8)$alkenyl, $(C_2\text{-}C_8)$alkynyl, $(C_4\text{-}C_8)$carbocyclylalkyl, optionally substituted aryl, optionally substituted heteroaryl, $—C(=O)(C_1\text{-}C_8)$alkyl, $—S(O)_n(C_1\text{-}C_8)$alkyl or aryl$(C_1\text{-}C_8)$alkyl; wherein each aryl or heteroaryl is independently optionally substituted with one or more Z groups;

or $R^{11}$ or $R^{12}$ taken together with a nitrogen to which they are both attached form a 3 to 7 membered heterocyclic ring wherein any one carbon atom of said heterocyclic ring can optionally be replaced with $—O^-$, —S— or $—NR^a—$, each Z group is independently halogen, $—O^-$, =O, $—OR^b$, $—SR^b$, $—S^-$, $—NR^b_2$, $—N^+R^b_3$, $=NR^b$, —CN, —OCN, —SCN, —N=C=O, —NCS, —NO, $—NO_2$, $=N_2$, $—N_3$, $—NHC(=O)R^b$, $—OC(=O)R^b$, $—NHC(=O)NR^b_2$, $—S(=O)_2—$, $—S(=O)_2OH$, $—S(=O)_2R^b$, $—OS(=O)_2OR^b$, $—S(=O)_2OH$, $—S(=O)R^b$, $—OP(=O)(OR^b)_2$, $—P(=O)(OR^b)_2$, $—P(=O)(O^-)_2$, $—P(O)(OR^b)(O^-)$, $—C(=O)R^b$, —C(=O)X, $—C(S)R^b$, $—C(O)OR^b$, $—C(O)O^-$, $—C(S)OR^b$, $—C(O)SR^b$, $—C(S)SR^b$, $—C(O)NR^b_2$, $—C(S)NR^b_2$, $—C(=NR^b)NR^b_2$, where in each $R^b$ is independently H, alkyl, aryl, arylalkyl or heterocycle; wherein one or more of the non-terminal carbon atoms of each said $(C_1\text{-}C_8)$alkyl is optionally replaced with —O—, —S— or $—NR^a—$.

In some embodiments, the composition of antiviral agent according to the present disclosure further comprises an antibiotic, a supplement, an anti-retroviral agent or combinations thereof. Examples of the antibiotics are penicillins (ampicillin plus sulbactam, piperacillin plus tazobactam, macrolides, cephalosporins, aminoglycosides and glycopeptides. In some embodiments, the antibiotic is selected from the group consisting of: currimycin and azithromycin.

In another aspect, the present disclosure also provides a composition of antiviral agent for use in prophylaxis or treatment of an infectious disease or a respiratory disease or an aerosolized composition of particles containing said composition of antiviral agent, which has a drug to lipid ratio of at least 0.01 mol/mol and optionally from 0.01 mol/mol to 2.0 mol/mol, 0.05 mol/mol to 2.0 mol/mol, 0.05 mol/mol to 1.5 mol/mol, 0.05 mol/mol to 1.0 mol/mol, 0.05 mol/mol to 0.5 mol/mol, 0.05 mol/mol to 0.3 mol/mol, 0.05 mol/mol to 0.2 mol/mol, 0.05 mol/mol to 0.15 mol/mol, 0.01 mol/mol to 1 mol/mol, 0.05 mol/mol to 0.1 mol/mol, 0.07 mol/mol to 0.09 mol/mol, or about 0.085 mol/mol; and a concentration of antiviral agent ranging from 0.1 mg/mL to 10 mg/mL.

In another aspect, the present disclosure also provides an aerosolized composition of particles comprising a liposomal quinine compound for use in prophylaxis or treatment of the respiratory disease according to the present disclosure, which has a drug-to-lipid ratio of at least 0.01 mol/mol, optionally at least 0.05 mol/mol, optionally from 0.01 mol/mol to 2.0 mol/mol, 0.05 mol/mol to 2.0 mol/mol, 0.05 mol/mol to 1.5 mol/mol, 0.05 mol/mol to 1.0 mol/mol, 0.05 mol/mol to 0.5 mol/mol, 0.05 mol/mol to 0.3 mol/mol, 0.05 mol/mol to 0.2 mol/mol, 0.05 mol/mol to 0.15 mol/mol, optionally about 0.5 mol/mol; and a concentration of quinine compound ranging from 1 mg/mL to 10 mg/mL on the basis of the composition.

In another aspect, the present disclosure also provides an aerosolized composition of particles comprising a liposomal nucleoside compound for use in prophylaxis or treatment of the infectious disease according to the present disclosure, which has a drug-to-lipid ratio of at least 0.01 mol/mol, optionally at least 0.05 mol/mol, optionally 0.01 mol/mol to 1 mol/mol, 0.03 mol/mol to 0.5 mol/mol, 0.03 mol/mol to 0.15 mol/mol, 0.03 mol/mol to 0.1 mol/mol, optionally about 0.05 mol/mol, 0.05 mol/mol to 0.5 mol/mol, 0.05 mol/mol to 0.15 mol/mol, 0.05 mol/mol to 0.1 mol/mol, 0.07 mol/mol to 0.1 mol/mol, optionally about 0.085 mol/mol; and a concentration of the nucleoside compound ranging from 0.1 mg/mL to 5 mg/mL on the basis of the composition.

In another aspect, the present disclosure also provides a nebulized spray comprising the composition of antiviral agent for use according to the present disclosure.

In another aspect, the present disclosure also provides an aerosolized composition of particles containing the composition of antiviral agent for use in prophylaxis or treatment of a respiratory disease or an infectious disease, which comprises the liposomal antiviral agent according to the present disclosure.

In another aspect, the present disclosure also provides a method for treating or preventing a respiratory disease or infectious disease, which comprises: administering an effective amount of the composition of antiviral agent for use in treatment or prophylaxis of respiratory disease according to the present disclosure to a subject in need thereof.

In another aspect, the present disclosure also provides a system for administering a composition of antiviral agent to a subject in need thereof. The system comprises the composition of antiviral agent according to the present disclosure and a pulmonary delivery device. The pulmonary delivery device is capable of aerosolizing the composition of antiviral agent, whereby after aerosolization formed particles containing the liposomal antiviral agent comprises free antiviral agent in an amount effective to provide immediate antiviral activity and the liposomal antiviral agent in an amount effective to provide sustained antiviral activity.

In another aspect, the present disclosure also provides a method for reducing complications associated with treatment of a respiratory disease or an infectious disease in a human subject for said complications, which comprises administering the composition according to the present disclosure to a subject in need thereof. According to the present disclosure, the complications include, but not limited to cardiotoxicity or hepatotoxicity. According to the present disclosure, the complications include, but not limited to prolongation of the corrected QT interval (QTc).

Other objectives, advantages and novel features of the disclosure will become more apparent from the following detailed description when taken in conjunction with the accompanying drawings.

DETAILED DESCRIPTION OF THE PREFERRED EMBODIMENTS

Figure 1:
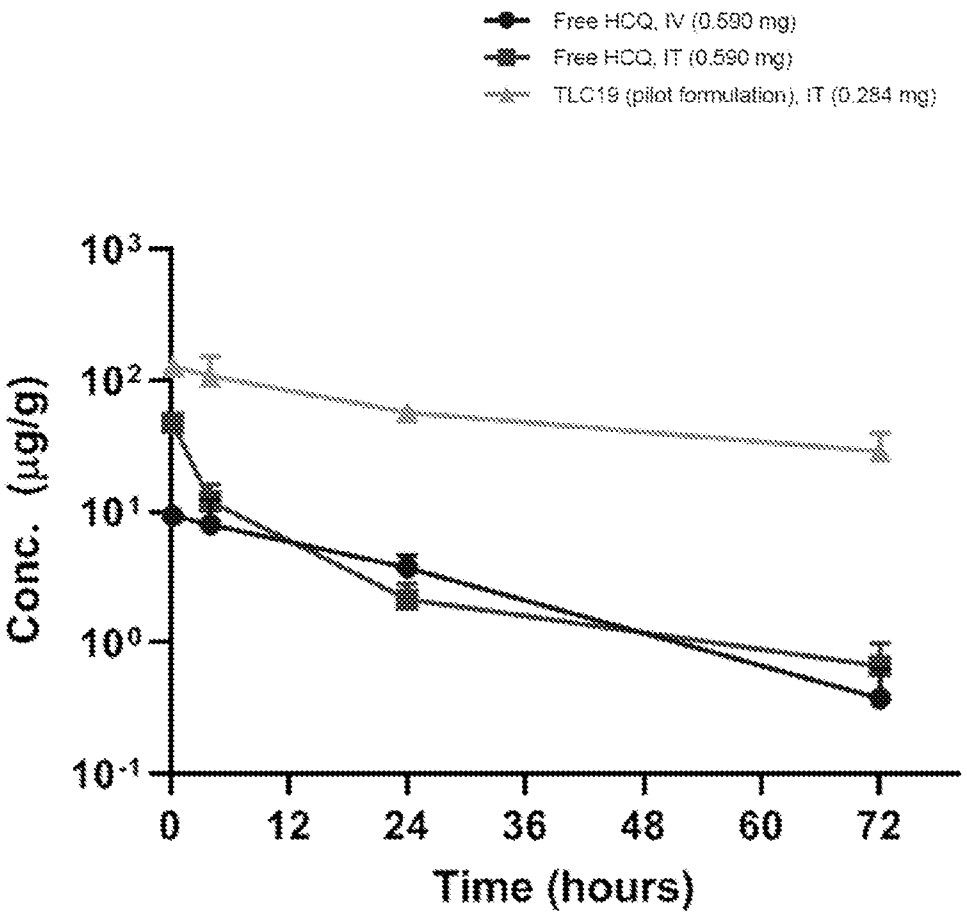
FIG. 1 depicting pharmacokinetic profiles of HCQ in rat lung following administration of the composition according to the present disclosure and free HCQ.

As employed above and throughout the disclosure, the following terms, unless otherwise indicated, shall be understood to have the following meanings.

As used herein, the singular forms “a”, “an” and “the” include the plural reference unless the context clearly indicates otherwise.

All numbers herein may be understood as modified by “about,” which, when referring to a measurable value such as an amount, a temporal duration, and the like, is meant to encompass variations of ±10%, preferably ±5%, more preferably ±1%, and even more preferably ±0.1% from the specified value, as such variations are appropriate to obtain a desired amount of liposomal drug, unless other specified.

The term “treating” “treated” or “treatment” as used herein includes preventive (e.g. prophylactic), palliative, and curative uses or results. The term “subject” includes a vertebrate having respiratory disease or other diseases or suspected to viral infection. Preferably, the subject is a warm-blooded animal, including mammals, preferably humans.

As used herein, the term “drug” refers to antiviral agent, such as quinine compound or nucleoside compound which pertains to an activity on desired therapeutic effect in accordance with the present disclosure. As used herein the term “drug to lipid ratio (D/L)” refers to the ratio of antiviral agent to at least one lipid in the composition according to the present disclosure. The drug content in a free form drug or liposomal drug of a composition of liposomal drug according to the present disclosure could, but not be limited to, be determined by UV-Vis absorbance measurements or high-pressure liquid chromatography (HPLC) method. The phospholipid content, or concentration, of liposome and liposomal drug could, but not be limited to, be determined by assaying the phosphorus content of liposome and liposomal drug samples using a phosphorus assay (adapted from G. Rouser et al., Lipids 1970, 5, 494-496) or HPLC method.

As used herein, while the pharmacokinetic data were obtained in rats, correlated pharmacokinetic profiles with the inhaled composition according to the present disclosure could be obtained in other mammals, including, but not limited to, cats, dogs, horses, mice, pigs, non-human primates and humans to develop the inhaled composition.

Infectious Diseases and Respiratory Diseases

Infectious disease and pathogenic infection hereby in the present disclosure refers to disorders caused by organism, such as viruses, parasites and bacteria. In one aspect, the infectious disease was transmitted via fecal-oral transmission, droplet contact, sexual transmission, oral transmission, direct contact, vehicle transmission, vertical transmission, iatrogenic transmission, or vector-borne transmission. In another aspect, the infectious disease could include, but not limited to, urinary tract infection, skin infection, respiratory infection, odontogenic infection, vaginal infection and intro-amniotic infection.

In some embodiments, the infectious diseases include, but not limited to: acute flaccid myelitis (AFM), anaplasmosis, anthrax, babesiosis, botulism, brucellosis, campylobacteriosis, carbapenem-resistant infection (CRE/CRPA), chancroid, chikungunya virus infection (chikungunya), chlamydia, ciguatera (harmful algae blooms (HABS)), *Clostridium difficile* infection, *Clostridium perfringens* (epsilon toxin), coccidioidomycosis fungal infection (valley fever), covid-19 (coronavirus disease 2019), creutzfeldt-jacob disease, transmissible spongiform encephalopathy (CJD), cryptosporidiosis (crypto), cyclosporiasis, dengue, 1,2,3,4 (dengue fever), diphtheria, *E. coli* infection, Shiga toxin-producing (STEC), eastern equine encephalitis (EEE), Ebola hemorrhagic fever (Ebola), ehrlichiosis, encephalitis, arboviral or parainfectious, enterovirus infection, non-polio (non-polio enterovirus), enterovirus infection D68 (EV-D68), giardiasis (giardia), glanders, gonococcal infection (gonorrhea), granuloma inguinale, haemophilus influenza disease, type b (HIB or h-flu), hantavirus pulmonary syndrome (HPS), hemolytic uremic syndrome (HUS), hepatitis A (Hep A), hepatitis B (Hep B), hepatitis C (Hep C), hepatitis D (Hep D), hepatitis E (Hep E), herpes, herpes Zoster, zoster VZV (shingles), histoplasmosis infection (histoplasmosis), human immunodeficiency virus/aids (HIV/AIDS), human papillomavirus (HPV), influenza (flu), lead poisoning legionellosis (legionnaires disease), leprosy (Hansens disease), leptospirosis, listeriosis (*listeria*), lyme disease, lymphogranuloma venereum infection (LGV), malaria, measles, melioidosis, meningitis, viral (meningitis, viral), meningococcal disease, bacterial (meningitis, bacterial), middle east respiratory syndrome coronavirus (MERS-CoV), multisystem inflammatory syndrome in children (MIS-C), mumps, norovirus, paralytic shellfish poisoning (paralytic shellfish poisoning, ciguatera), pediculosis (lice, head and body lice), pelvic inflammatory disease (PID), pertussis (whooping cough), plague; bubonic, septicemic, pneumonic (plague), pneumococcal disease (pneumonia), poliomyelitis (polio), powassan, psittacosis (parrot fever), pthiriasis (crabs; pubic lice infestation), pustular rash diseases (small pox, monkeypox, cowpox), Q-fever, rabies, ricin poisoning, rickettsiosis (rocky mountain spotted fever), rubella, including congenital (german measles), *salmonellosis* gastroenteritis (*salmonella*), scabies infestation (scabies), scombroid, septic shock (sepsis), severe acute respiratory syndrome (SARS), shigellosis gastroenteritis (*shigella*), smallpox, staphyloccal infection, methicillin-resistant (MRSA), staphylococcal food poisoning, enterotoxin—B poisoning (Staph food poisoning), staphylococcal infection, vancomycin intermediate (VISA), staphylococcal infection, vancomycin resistant (VRSA), streptococcal disease, group a (invasive) (strep A (invasive)), streptococcal disease, group b (Strep-B), streptococcal toxic-shock syndrome, stss, toxic shock (STSS, TSS), syphilis, primary, secondary, early latent, late latent, congenital, tetanus infection, *tetani* (lock jaw), trichomoniasis (*trichomonas* infection), trichinosis infection (trichinosis), tuberculosis (TB), tuberculosis (latent) (LTBI), tularemia (rabbit fever), typhoid fever (group D), typhus, vaginosis, bacterial (yeast infection), vaping-associated lung injury (E-cigarette associated lung injury), varicella (chickenpox), *Vibrio cholerae* (cholera), vibriosis (*vibrio*), viral hemorrhagic fever (Ebola, LASSA, Marburg), West Nile virus infection, yellow fever, Yersenia (*Yersinia*), and Zika virus infection (Zika).

Respiratory diseases in accordance with the present disclosure include, but are not limited to: acute respiratory distress syndrome (ARDS), acute lung injury (ALI) or severe acute respiratory syndrome (SARS) with main complications including: fluid leaks into the lungs making breathing difficult or impossible. Symptoms typically include fever, cough, productive cough, nonproductive cough, dyspnea and fatigue or myalgia, tightness in the chest, and gradual onset of shortness of breath. Complications include pulmonary hypertension, heart failure, pneumonia, or pulmonary embolism.

In some embodiments, the composition of the antiviral agent in accordance with the present disclosure is suitable for use in prophylaxis as prevention, treatment of mild cases, treatment of acute respiratory distress syndrome (ARDS), acute lung injury (ALI) or severe acute respiratory syndrome (SARS) caused by coronavirus or the derivatives thereof.

Liposome and Liposomal Antiviral Agents

The term “liposome” or “liposomal” as used herein are directed to a population of vesicles, each vesicle being characterized by having an aqueous interior space sequestered from an outer medium by a membrane of one or more bilayer membranes. Bilayer membranes of liposomes are typically formed by one or more lipids, i.e., amphiphilic molecules of synthetic or natural origin that comprise spatially separated hydrophobic and hydrophilic domains.

The interior aqueous space of the liposome is substantially free of a neutral lipid, such as triglyceride, non-aqueous phase (oil phase), water-oil emulsions, a second liposome or other mixtures containing non-aqueous phase. Non-limiting examples of liposomes include small unilamellar vesicles (SUV) and large unilamellar vesicles (LUV), and multi-lamellar vesicles (MLV) with an average diameter ranges from 50 nm to 10000 nm, 50 nm to 500 nm, 50 nm to 450 nm, 50 nm to 400 nm, 50 nm to 350 nm, 50 nm to 300 nm, 50 nm to 250 nm, 50 nm to 200 nm, 100 nm to 500 nm, 100 nm to 450 nm, 100 nm to 400 nm, 100 nm to 350 nm, 100 nm to 300 nm, 100 nm to 250 nm, or 100 nm to 200 nm, which are capable of passing through sterile filters. For example, the MLV can be directly formed by a hydrated lipid film, spray-dried powder or lyophilized cake of selected lipid compositions with trapping agent; the SUV and LUV can be sized from MLV by sonication, homogenization, microfluidization or extrusion.

In general, liposomes comprise a lipid mixture typically including at least one lipid selected from the group consisting of: dialiphatic chain lipids, such as phospholipids, diglycerides, dialiphatic glycolipids; single lipids such as sphingomyelin and glycosphingolipid; sterols such as cholesterol; and derivates thereof, and combinations thereof.

Examples of phospholipids according to the present disclosure include, but are not limited to, 1,2-dilauroyl-sn-glycero-3-phosphocholine (DLPC), 1,2-dimyristoyl-sn-glycero-3-phosphocholine (DMPC), 1,2-dipalmitoyl-sn-glycero-3-phosphocholine (DPPC), 1-palmitoyl-2-stearoyl-sn-glycero-3-phosphocholine (PSPC), 1-palmitoyl-2-oleoyl-sn-glycero-3-phosphatidylcholine (POPC), 1,2-distearoyl-sn-glycero-3-phosphocholine (DSPC), 1,2-dioleoyl-sn-glycero-3-phosphocholine (DOPC), hydrogenated soy phosphatidylcholine (HSPC), 1,2-dimyristoyl-sn-glycero-3-phospho-(1'-rac-glycerol) (sodium salt) (DMPG), 1,2-dipalmitoyl-sn-glycero-3-phospho-(1'-rac-glycerol) (sodium salt) (DPPG), 1-palmitoyl-2-stearoyl-sn-glycero-3-phospho-(1'-rac-glycerol) (sodium salt) (PSPG), 1,2-distearoyl-sn-glycero-3-phospho-(1'-rac-glycerol) (sodium salt) (DSPG), 1,2-dioleoyl-sn-glycero-3-phospho-(1'-rac-glycerol) (DOPG), 1,2-dimyristoyl-sn-glycero-3-phospho-L-serine (sodium salt) (DMPS), 1,2-dipalmitoyl-sn-glycero-3-phospho-L-serine (sodium salt) (DPPS), 1,2-distearoyl-sn-glycero-3-phospho-L-serine (sodium salt) (DSPS), 1,2-dioleoyl-sn-glycero-3-phospho-L-serine (DOPS), 1,2-dimyristoyl-sn-glycero-3-phosphate (sodium salt) (DMPA), 1,2-dipalmitoyl-sn-glycero-3-phosphate (sodium salt) (DPPA), 1,2-distearoyl-sn-glycero-3-phosphate (sodium salt) (DSPA), 1,2-dioleoyl-sn-glycero-3-phosphate (sodium salt) (DOPA), 1,2-dipalmitoyl-sn-glycero-3-phosphoethanolamine (DPPE), 1-palmitoyl-2-oleoyl-sn-glycero-3-phosphoethanolamine (POPE), 1,2-distearoyl-sn-glycero-3-phosphoethanolamine (DSPE), 1,2-dioleoyl-sn-glycero-3-phosphoethanolamine (DOPE), 1,2-dipalmitoyl-sn-glycero-3-phospho-(1'-myo-inositol) (ammonium salt) (DPPI), 1,2-distearoyl-sn-glycero-3-phosphoinositol (ammonium salt) (DSPI), 1,2-dioleoyl-sn-glycero-3-phospho-(1'-myo-inositol) (ammonium salt) (DOPI), cardiolipin, L-α-phosphatidylcholine (EPC), and L-α-phosphatidylethanolamine (EPE).

The liposomal antiviral agent according to the present disclosure optionally incorporates a significant amount of polyethylene glycol (PEG) moiety onto the surface of the vesicles by incorporating a PEG-modified phosphatidylethanolamine (PE) into the membrane of the vesicles to achieve longer, sustained drug release that will be safe, efficacious, and less frequent dosing.

The liposomal antiviral agent according to the present disclosure optionally incorporates a significant amount of negative charge moiety onto the surface of the vesicles by incorporating a PEG-modified phosphatidylethanolamine (PE) or fatty acids into the membrane of the vesicles to prevent liposome aggregation or flocculation processes in solution during storage.

The polyethylene glycol-modified lipid comprises a polyethylene glycol moiety conjugated with a lipid. In some embodiments, the PEG moiety has a molecular weight from about 5,00 to about 20,000 daltons. In a particular embodiment, the PEG-modified lipid is mixed with the phospholipids to form liposomes with one or more bilayer membranes. In some embodiments, the amount of PEG-modified lipid ranges from 0.0001 mol % to 40 mol %, optionally from 0.001 mol % to 30 mol %, optionally from 0.01 mol % to 20 mol %, optionally from 0.0001 mol % to 10 mol %, optionally from 0.001 mol/% to 5 mol %, and particularly no more than 6 mol %, optionally 5 mol %, 3 mol % or 2 mol %, on the basis of the total phospholipids and sterol. In some embodiments, the PEG-modified lipid has a PEG moiety with an average molecular weight ranging from 1,000 g/mol to 5,000 g/mol. In a particular embodiment, the PEG-modified lipid is phosphatidylethanolamine linked to a polyethylene glycol group (PE-PEG). In further embodiments, PEG-modified phosphatidylethanolamine is 1,2-distearoyl-sn-glycero-3-phosphoethanolamine-N-[methoxy(polyethylene glycol)] (DSPE-PEG).

In a particular embodiment, the PEG-modified phosphatidylethanolamine (PE) is DSPE-PEG at an amount ranging from 0.0001 mol % to 40 mol %, optionally from 0.01 mol % to 20 mol %, of the total lipid content of the liposomes and has a PEG moiety with an average molecular weight of 2,000 g/mol.

The terms "liposomal antiviral agent" and "liposomal drug" are interchangeably used in the present disclosure. The liposomal antiviral agent in accordance to the present disclosure comprises liposomes with entrapped antiviral agent, which are prepared by encapsulating the antiviral agent in the aqueous interior of the liposome via a transmembrane pH gradient-driven remote loading method.

In some embodiments, the liposomes are formed together with a drug substance, such as hydroxychloroquine or GS-441524, to encapsulate the drug substance in the aqueous interior of the liposome or alone as empty liposomes having a transmembrane gradient for later use in a drug loading process as active loading method, also known as remote loading, to form the liposomal drug.

In some embodiments, the transmembrane pH gradient is created by using a trapping agent for remote loading of the antiviral agent into liposome and the trapping agent is composed of an ammonium compound and an anionic counterion.

The term "ammonium compound" includes non-substituted or substituted ammonium being a cationic ion presented by $NR_4^+$, wherein each R is independently H or an organic residue, and the organic residue is independently alkyl, alkylidene, heterocyclic alkyl, cycloalkyl, aryl, alkenyl, cycloalkenyl, or a hydroxyl-substituted derivative thereof, optionally including within its hydrocarbon chain a S, O, or N atom, forming an ether, ester, thioether, amine, or amide bond. In one embodiment, the ammonium compound is ammonium.

The term "anionic counterion" refers to an anionic ion or an entity which is covalently linked to one anionic functional group. The anionic ion or the anionic functional group has negative electric charge under physiological environment.

The anionic ion or the anionic functional group can be selected from one or more of the following: sulfate, citrate, sulfonate, phosphate, pyrophosphate, tartrate, succinate, maleate, borate, carboxylate, bicarbonate, glucuronate, chloride, hydroxide, nitrate, cyanate or bromide.

In one embodiment, the anionic ion and the anionic functional group is selected from one or more of the following: citrate, sulfate, sulfonate, phosphate, pyrophosphate and carboxylate.

In yet another embodiment, the entity linked to the anionic functional group can be a natural or synthetic, organic or inorganic compound. Examples of the entity include, but are not limited to, a non-polymer substance selected from alkyl group or aryl group, such as benzene, nucleotide and saccharide. The alkyl refers to a saturated hydrocarbon radical having indicated number of carbon atoms. For example, the alkyl is selected from the group consisting of alkyl of 1 to 4 carbons ($C_{1-4}$ alkyl), alkyl of 1 to 6 carbons ($C_{1-6}$ alkyl), alkyl of 1 to 8 carbons ($C_{1-8}$ alkyl), alkyl of 1 to 10 carbons ($C_{1-10}$ alkyl), alkyl of 1 to 12 carbons ($C_{1-12}$ alkyl), alkyl of 1 to 14 carbons ($C_{1-14}$ alkyl), alkyl of 1 to 16 carbons ($C_{1-16}$ alkyl), alkyl of 1 to 18 carbons ($C_{1-18}$ alkyl) and alkyl of 1 to 20 carbons ($C_{1-20}$ alkyl).

In some embodiments, the anionic counterion is selected from the group consisting of sulfate, phosphate, citrate, gluconate, sucrose octasulfate, dextran sulfate and combinations thereof.

In some embodiments, the trapping agent is selected from the group consisting of ammonium sulfate, ammonium phosphate, ammonium citrate, ammonium sucrose octasulfate, ammonium dextran sulfate, dimethylammonium sulfate, dimethylammonium phosphate, dimethylammonium citrate, diethylammonium sulfate, diethylammonium phosphate, diethylammonium citrate, diethylammonium sucrose octasulfate, diethylammonium dextran sulfate, trimethylammonium sulfate, trimethylammonium phosphate, trimethylammonium citrate, triethylammonium sulfate, triethylammonium phosphate, triethylammonium citrate, triethylammonium sucrose octasulfate, triethylammonium dextran sulfate, copper gluconate, copper glucuronate and combinations thereof.

In some embodiments, the liposomal antiviral agent has a mean particle diameter between 50 nm and 1,000 nm. Non-limiting examples of the liposomal antiviral agent has an average diameter ranges from 50 nm to 20 μm, 50 nm to 10 μm, 50 nm to 1000 nm, 50 nm to 500 nm, 50 nm to 400 nm, 50 nm to 300 nm, 50 nm to 250 nm, 50 nm to 200 nm, 100 nm to 300 nm or 150 nm to 250 nm.

In some embodiments, the antiviral agent includes, but not be limited to, antimalarial agent, antiretroviral agent or combination thereof. Particularly, the antiviral agent is selected from the group consisting of quinine compound, nucleoside compound and combination thereof.

The term "quinine compound" refers to a substance derived from a lead compound with anti-malarial activity, quinine, extracted from the bark of the cinchona tree. Quinine compounds, such as hydroxychloroquine, have been shown to be potential in inhibiting exacerbation of pneumonia, improving imaging findings, promoting virus negative conversion, and shortening the disease course. However, systemic administration of quinine compound could show side effects such as blurred vision, nausea, vomiting, abdominal cramps, headache, and diarrhea.

The quinine compound according to the present disclosure includes but not be limited to quinine and other 4-aminoquinolines, such as quinine, quinidine, cinchonine, cinchonidine, chloroquine (CQ), hydroxychloroquine (HCQ) and the like. Exemplary quinine compounds, CQ and HCQ, are suggested to be able to prevent the acidification of intracellular organelles and inhibit lysosomal release of viral genome. In addition, these drugs can interfere with the glycosylation of the angiotensin-converting enzyme-2 (ACE2) receptor on the host cell and reduce binding efficiency between the receptor and spike protein on the surface of the coronavirus.

Nucleosides as inhibitors of nonstructural viral protein, such as RNA-dependent RNA polymerase, being used as potential therapies for RNA virus infections have been reported. The nucleosides are expected to be taken up by the cell and converted in vivo to a triphosphate to compete for the polymerase nucleotide binding site to terminate a polymerase chain reaction. This conversion to the triphosphate is commonly mediated by cellular kinases which imparts additional structural requirements on a potential nucleoside polymerase inhibitor. Formation of the monophosphate by a nucleoside kinase is generally considered as the rate limiting step of the three phosphorylation events. U.S. Pat. No. 7,964,580 discloses pronucleosides containing phosphoramidate moiety which are masked with neutral lipophilic groups to obtain a suitable partition coefficient to optimize uptake and transport into the cell dramatically enhancing the intracellular concentration of the nucleoside monophosphate relative to administering the parent nucleoside alone. While there are controversial observations foreseeing the enzyme-mediated hydrolysis of the phosphate ester moiety probably produces a nucleoside itself instead of a target nucleoside monophosphate immediately after circulation before its targeting to the desired site. For instances, via intravenous administration, (2R,3R,4S,5R)-2-(4-aminopyrrolo[2,1-f][1,2,4]triazin-7-yl)-3,4-dihydroxy-5-(hydroxymethyl) oxolane-2-carbonitrile (also known as GS-441524), known nucleoside compound, is a more stable metabolite of remdesivir than its monophosphate form (Humeniuk R, Mathias A, Cao H, et al. Safety, Tolerability, and Pharmacokinetics of Remdesivir, An Antiviral for Treatment of COVID-19, in Healthy Subjects. Clin Trans' Sci. 2020; 13(5):896-906. doi:10.1111/cts.12840). An efficient delivery of the nucleoside compound to a target cellular site enriched with the critical rate limiting nucleoside kinase could be a universal platform solution for avoiding complicated manufacture process of different pronucleosides of a large spectrum of nucleoside compounds.

In some embodiments, the composition of antiviral agent according to the present disclosure further comprises an antibiotic, a supplement, or combinations thereof.

In some embodiments, the antiviral agent comprises one or more l'-substituted carba-nucleoside compounds or 2'-substituted carba-nucleoside compounds as described in the U.S. Pat. Nos. 8,008,264 and 9,481,704.

In some embodiments, the antiviral agent is directed to nucleoside compounds include but not be limited to 1'-substituted carba-nucleoside compound and pharmaceutically acceptable salt thereof.

In some embodiments, the antiviral agent comprises an inhibitor of RNA-dependent RNA viral polymerase, wherein the inhibitor includes nucleoside compound of structural formula (I), (I)

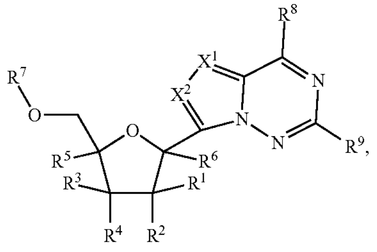

each $R^1$, $R^2$ $R^3$, $R^4$ or $R^5$ is independently H, $OR^a$, $N(R^a)_2$, $N_3$, CN, $NO_2$, $S(O)_nR^a$, halogen or methyl, wherein n is 0, 1 or 2;

$R^6$ is CN or H;

each $R^a$ is independently H, $(C_1\text{-}C_8)$alkyl, $(C_2\text{-}C_8)$alkenyl, $(C_2\text{-}C_8)$alkynyl, aryl$(C_1\text{-}C_8)$alkyl, $(C_4\text{-}C_8)$carbocyclylalkyl, $—C(=O)R^{11}$, $—C(=O)OR^{11}$, $—C(=O)NR^{11}R^{12}$, $—C(=O)SR^{11}$, $—S(O)R^{11}$, $—S(O)_2R^{11}$, $—S(O)(OR^{11})$, $—S(O)_2(OR^{11})$, or $—SO_2NR^{11}R^{12}$; and $R^7$ is H;

Each $X^1$ or $X^2$ is independently $C—R^{10}$ or N;

$R^8$ is halogen, $NR^{11}R^{12}$, $N(R^{11})(OR^{11})$, $NR^{11}NR^{11}R^{12}$, $N_3$, NO, $NO_2$, CHO, CN, $—CH(=NR^{11})$, $—CH=NHNR^{11}$, $—CH=N(OR^{11})$, $—CH(OR^{11})_2$, $—C(=O)NR^{11}R^{12}$, $—C(=S)NR^{11}R^{12}$, $—C(=O)OR^{11}$, $(C_1\text{-}C_8)$alkyl, $(C_2\text{-}C_8)$alkenyl, $(C_2\text{-}C_8)$alkynyl, aryl$(C_1\text{-}C_8)$alkyl, $(C_4\text{-}C_8)$carbocyclylalkyl, optionally substituted aryl, optionally substituted heteroaryl, $—C(=O)(C_1\text{-}C_8)$alkyl, $—S(O)_n(C_1\text{-}C_8)$alkyl, aryl$(C_1\text{-}C_8)$alkyl, $OR^{11}$ or $SR^{11}$;

wherein each aryl or heteroaryl is independently optionally substituted with one or more Z groups;

each $R^9$ or $R^{10}$ is independently H, halogen, $R^{11}$, $OR^{11}$, $SR^{11}$, $NR^{11}R^{12}$, $N(R^{11})(OR^{11})$, $NR^{11}NR^{11}R^{12}$, $N_3$, NO, $NO_2$, CHO, CN, $—CH(=NR^{11})$, $—CH=NHNR^{11}$, $—CH=N(OR^{11})$, $—CH(OR^{11})_2$, $—C(=O)NR^{11}R^{12}$, $—C(=S)NR^{11}R^{12}$, $—C(=O)OR^{11}$;

each $R^{11}$ or $R^{12}$ is independently H, $(C_1\text{-}C_8)$alkyl, $(C_2\text{-}C_8)$alkenyl, $(C_2\text{-}C_8)$alkynyl, $(C_4\text{-}C_8)$carbocyclylalkyl, optionally substituted aryl, optionally substituted heteroaryl, $—C(=O)(C_1\text{-}C_8)$alkyl, $—S(O)_n(C_1\text{-}C_8)$alkyl or aryl$(C_1\text{-}C_8)$alkyl; wherein each aryl or heteroaryl is independently optionally substituted with one or more Z groups;

or $R^{11}$ or $R^{12}$ taken together with a nitrogen to which they are both attached form a 3 to 7 membered heterocyclic ring wherein any one carbon atom of said heterocyclic ring can optionally be replaced with —O—, —S— or $—NR^a—$, each Z group is independently halogen, $—O^-$, =O, $—OR^b$, $—SR^b$, $—S^-$, $—NR^b_2$, $—N^+R^b_3$, $=NR^b$, —CN, —OCN, —SCN, —N=C=O, —NCS, —NO, $—NO_2$, $=N_2$, $—N_3$, $—NHC(=O)R^b$, $—OC(=O)R^b$, $—NHC(=O)NR^b2$, $—S(=O)_2—$, $—S(=O)_2OH$, $—S(=O)_2R^b$, $—OS(=O)_2OR^b$, $—S(=O)_2OH$, $—S(=O)R^b$, $—OP(=O)(OR^b)_2$, $—P(=O)(OR^b)_2$, $—P(=O)(O—)_2$, $—P(O)(OR^b)(O—)$, $—C(=O)R^b$, —C(=O)X, $—C(S)R^b$, $—C(O)OR^b$, —C(O)O—, $—C(S)OR^b$, $—C(O)SR^b$, $—C(S)SR^b$, $—C(O)NR^b_2$, $—C(S)NR^b_2$, $—C(=NR^b)NR^b_2$, where in each $R^b$ is independently H, alkyl, aryl, arylalkyl or heterocycle; wherein one or more of the non-terminal carbon atoms of each said $(C_1\text{-}C_8)$alkyl is optionally replaced with —O—, —S— or $—NR^a—$.

In some embodiments, the antiviral agent is selected from the group consisting of:

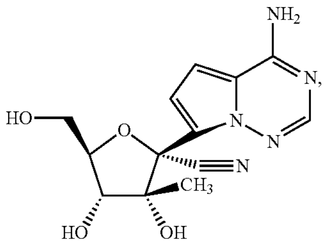

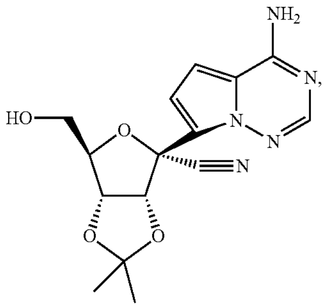

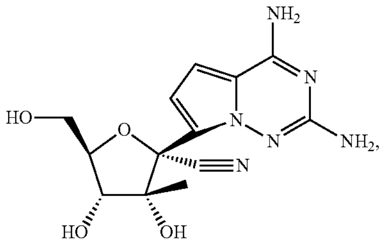

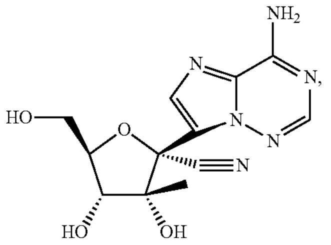

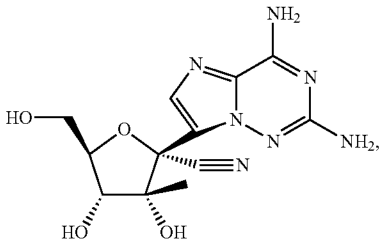

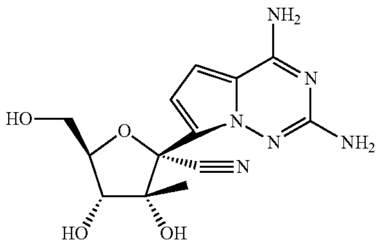

-continued

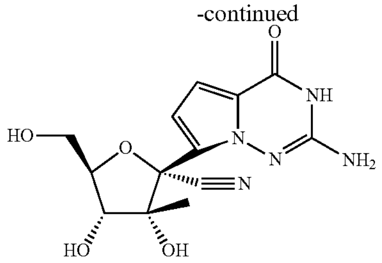

or a pharmaceutically acceptable salt thereof.

In one aspect, the liposomal antiviral agent comprises: a lipid bilayer comprising: one or more phospholipids, a sterol, and an optional polyethylene glycol (PEG)-modified lipid, particularly to PEG-modified phosphatidylethanolamine (PEG-PE); and an aqueous interior encompassed by the lipid bilayer and containing one or more antiviral agents.

In an embodiment, the one or more phospholipids is neutral phospholipid, and the PEG-modified lipid is DSPE-PEG. The amount of DSPE-PEG ranges from 0.001 to 5 mol %, optionally from 0.0001 mol % to 40 mol %, optionally less than 6 mol %, optionally ranges from 0.001 mol % to 30 mol % on the basis of the total phospholipids and sterol.

In one embodiment, the composition of liposomal antiviral agent has a drug to lipid ratio (ratio of the antiviral agent to at least one lipid) being at least 0.01 mol/mol to 0.1 mol/mol and comprises: a lipid bilayer comprising: DPPC, cholesterol; and an aqueous interior encompassed by the lipid bilayer and containing the antiviral agent entrapped by a trapping agent, wherein the antiviral agent is (2R,3R,4S,5R)-2-(4-aminopyrrolo[2,1-f][1,2,4]triazin-7-yl)-3,4-dihydroxy-5-(hydroxymethyl) oxolane-2-carbonitrile (GS-441524) and the trapping agent is ammonium sulfate.

Inhalable Composition and the Aerosolized Particles Thereof

The composition of antiviral agent in accordance with the present disclosure is adapted to preparation of an inhalable aerosolized composition of particles containing the liposomal antiviral agent as previously described. The composition can be administered for inhalation either as a nebulized spray or aerosol, or by intrathecal administration. Inhalation administrations are preferred. The overall result is a less frequent administration and an enhanced therapeutic index compared to free drug or parenteral form of the drug. The liposomal antiviral agent in the composition is particularly advantageous due to their ability to protect the drug while being compatible with the lung lining or lung surfactant.

In one embodiment, the composition of antiviral agent according to the present disclosure has a drug to lipid ratio (D/L) at least 0.01 mol/mol, optionally at least 0.1 mol/mol, and preferably ranging from 0.05 mol/mol to 1 mol/mol, optionally 0.1 mol/mol to 0.7 mol/mol, optionally 0.15 mol/mol to 0.6 mol/mol and optionally 0.15 mol/mol to 0.2 mol/mol. The drug to lipid ratio refers to the molar ratio of the antiviral agent to at least one lipid. In particular embodiments, the at least one lipid comprises a neutral phospholipid and a sterol at a molar ratio of 1:1 or 3:2. Optionally, the neutral phospholipid is DPPC and the sterol is cholesterol.

In one embodiment, the composition of antiviral agent has the at least one lipid at a concentration ranging from 1 mM to 200 mM, from 1 mM to 100 mM, 5 mM to 100 mM, from 10 mM to 180 mM, from 15 mM to 140 mM, from 20 to 160 mM, from 30 mM to 140 mM, and from 40 mM to 120 mM.

Alternatively, the composition of antiviral agent has the one or more phospholipids at a concentration ranging from 1 mM to 100 mM, 5 mM to 100 mM, from 5 mM to 90 mM, from 10 mM to 80 mM, from 15 mM to 70 mM or from 20 mM to 60 mM.

In one embodiment, the composition of antiviral agent has a total concentration of the quinine compound ranging from 0.1 mg/mL to 80 mg/mL, from 0.5 mg/mL to 60 mg/mL, from 1 to 30 mg/mL and from 2 mg/mL to 15 mg/mL, from 0.5 mg/mL to 70 mg/mL, from 0.5 mg/mL to 60 mg/mL, from 0.5 mg/mL to 50 mg/mL, from 0.5 mg/mL to 40 mg/mL, from 0.5 mg/mL to 30 mg/mL, from 0.5 mg/mL to 20 mg/mL, from 0.5 mg/mL to 10 mg/mL, from 0.5 mg/mL to 8 mg/mL, 0.5 mg/mL to 5 mg/mL, from 1.0 mg/mL to 6 mg/mL, from 1.5 mg/mL to 5.0 mg/mL, from 1.5 mg/mL to 4.0 mg/mL or about 2.0 mg/mL.

In one embodiment, the composition of antiviral agent has the one or more phospholipids at a concentration ranging from 1 mM to 100 mM, 5 mM to 100 mM, from 5 mM to 90 mM, from 10 mM to 80 mM, from 15 mM to 70 mM or from 20 mM to 60 mM; and the drug-to-lipid (D/L) ratio ranges from 0.01 mol/mol to 1 mol/mol, 0.03 mol/mol to 0.5 mol/mol, 0.03 mol/mol to 0.15 mol/mol, 0.03 mol/mol to 0.1 mol/mol, about 0.005 mol/mol, 0.05 mol/mol to 0.1 mol/mol, 0.07 mol/mol to 0.09 mol/mol, or 0.085 mol/mol, wherein the antiviral agent is a 1'-substituted carba-nucleoside compound, 2'-substituted carba-nucleoside compound having a free 5'-OH group.

In some embodiments, the composition of liposomal antiviral agent further has a free form antiviral agent and the free form antiviral agent of the composition according to the present disclosure is at an amount less than 60%, 50%, 45%, 40%, 35%, 30%, 25%, 20%, 15%, 10%, 5%, or at a range from 10% to 40%, from 15% to 35%, or from 10% to 30% of the total amount of the antiviral agent of the composition.

In some embodiments, aerosolized composition of particles containing the composition of the present disclosure is generated by aerosolizing the composition with a nebulizer, which is selected from the group consisting of air-jet nebulizer, ultrasonic nebulizer, a vibrating mesh nebulizer, a condensation aerosol generator, an electro-hydrodynamic nebulizer or other pulmonary delivery device known in the art.

In some embodiments, the aerosolized composition of particles has a mass median aerodynamic diameter between 0.5 μm and 5 μm, and optionally 1 μm and 3 μm.

After aerosolization, leakage of the antiviral agent from the liposome of the liposomal antiviral agent in the composition according to the present disclosure leads a portion of the antiviral agent to become in a free form, not entrapped by the liposome. The resultant free form antiviral agent in the aerosolized composition is less than 60%, 50%, 40%, 30%, 20%, 10% or 5%; optionally at a controlled percentage ranging from 0.1% to 50%, 0.5% to 40%, 0.5% to 30%, 0.5% to 20%, 0.5% to 10%, 0.5% to 5%, 10% to 50%, 15% to 45%, 20% to 45%, 25% to 35%.

In a specific embodiment, the aerosolized composition of particles is subjected to pulmonary delivery to a subject in need to perform a release rate between about 0.5% and 25% of the administered drug dose per hour with complete release of the antiviral agent occurring after a minimum of about 12 to 24 hours.

The disclosure will be further described with reference to the following specific, non-limiting examples.

EXAMPLES

The following examples illustrate the preparation and properties of certain embodiments of the present disclosure.

Example 1 Stability of the Liposomal Antiviral Agent

The liposomal antiviral agent in accordance to the present disclosure comprises liposomes with entrapped antiviral agent, which were prepared by active loading or passive loading as known in the art.

A. Preparation of Liposomal Antiviral Agent by Active Loading

I. Preparation of Empty Liposomes

The process of preparing empty liposomes for remote loading was performed by thin-film hydration method or solvent injection, which could comprise the following steps:

1. weighing out lipid mixture of phospholipids, cholesterol at a predetermined molar ratio in the presence or absence of DSPE-PEG2000 and adding them to 10 mL of chloroform in a round-bottom flask;
2. placing the flask in a rotary evaporator at suitable temperature depending on the lipid composition and stirring the flask to dissolve the lipid mixture, followed by putting the flask under vacuum while stirring to evaporate off the chloroform to obtain a dried lipid film;
3. preparing a trapping agent solution (e g ammonium sulfate (A.S.)) by adding a trapping agent to distilled water and vortexing the solution to dissolve powders;
4. adding the trapping agent solution to the dried lipid film and stirring it at suitable temperature depending on the lipid composition to form a liposome solution;
5. freeze-thawing the liposome solution for with liquid nitrogen and suitable temperature depending on the lipid composition by water bath to obtain a liposome sample;
6. extruding obtained liposome sample through 0.2 μm polycarbonate membrane, 0.1 μm polycarbonate membrane at suitable temperature depending on the lipid composition to get the designed particle size;
7. dialyzing the extruded liposome sample to remove free trapping agent, followed by adding the sample to a dialysis bag (MWCO: 25 kD), sealing the bag, and stirring the dialysis bag in 100×volume of a 9.4% (w/v) sucrose solution or saline or suitable buffer; and further replacing the sucrose solution or saline or suitable buffer after 1 hour, 4 hours, and let it stir overnight; and
8. sterilizing the dialyzed liposome sample by filtering it through a 0.45 μm PTFE membrane to obtain the empty liposomes.

II. Drug Loading of Antiviral Agent into Liposome to Obtain Liposomal Antiviral Agent The following method represents a typical protocol for the encapsulation of hydroxychloroquine or chloroquine in liposome by remote loading, which comprises steps of:

1. preparing a solution of 40 mg/mL or suitable concentration of hydroxychloroquine or chloroquine in 9.4% (w/v) sucrose or suitable medium and briefly heating it at suitable temperature to obtain a stock solution containing hydroxychloroquine or chloroquine (hereafter denoted as stock solution);
2. mixing together empty liposomes as prepared by the process according to Example 1, section A (I) [in a typical embodiment, with the condition of: DPPC:cholesterol at a molar ratio of 3:2, 300 mM ammonium sulfate (A.S.), and 30 mM phospholipid concentration], a saline solution, and the stock solution into a conical tube to obtain a loading solution, targeting a D/L ratio to be 100 g/mol or 0.19 mol/mol;

3. continuously shaking the loading solution at a suitable temperature for 30 minutes or a designed time period to form the sample of drug loaded liposomes;

4. removing the free drug or changing the buffer or adjusting the drug concentration by dialysis method or membrane-based Tangential Flow Filtration (TFF) if necessary;

5. determining the drug encapsulation (i.e. loading efficiency) of the final sample using size-exclusion column chromatography and HPLC analysis to obtain a composition of liposomal antiviral agent at a concentration of drug ranging from 2 mg/mL to 10 mg/mL and the antiviral agent to lipid at a ratio of 0.05 mol/mol to 1.5 mol/mol (See below Formulation #1 to #3) on the basis of the whole composition.

| Formulation | #1 | #2 | #3 |
|---|---|---|---|
| HCQ (mg/ml) | 2.95 | 6.06 | 9.70 |
| HCQ (mM) | 6.80 | 13.96 | 22.35 |
| DPPC (mM) | 30.0 | 30.0 | 30.0 |
| Cholesterol (mM) | 20.0 | 20.0 | 20.0 |
| Total lipid (mM) | 50 | 50 | 50 |
| D/L (by total lipid) | 0.136 | 0.279 | 0.447 |

B. Preparation of Liposomal Antiviral Agent by Passive Loading

Liposomes could be prepared via the thin-film hydration method or solvent injection method. The process for preparing liposomal antiviral agent by solvent injection method is embodied by the method comprising the following steps:

1. weighing out lipid mixture of phospholipids, cholesterol at a predetermined molar ratio in the presence or absence of DSPE-PEG2000 and adding them to 10 mL of ethanol in a flask to form a solvent phase containing the lipids;

2. preparing the hydroxychloroquine or chloroquine solution in 0.9% sodium chloride (saline) or suitable medium in a concentration from 40 mg/mL to 60 mg/mL or suitable concentration to form a water phase;

3. pre-warming 40 mL of the indicated water phase (40 mg/mL hydroxychloroquine) at 50° C. for at least 30 minutes;

4. adding the dissolved lipid mixture, i.e. solvent phase, by syringe into the pre-warmed water phase under stirring to form pro-liposome sample and then keep stirring the pro-liposome sample at 50° C. for 5 minutes;

5. extruding the pro-liposome sample through 0.2 μm polycarbonate membrane at suitable temperature depending on the lipid composition to get the designed particle size;

6. diafiltrating the extruded liposome sample to remove free drug substance with saline (0.9% NaCl); and 7. sterilizing the diafiltrated liposome sample by filtering it through a 0.2 μm polycarbonate membrane to obtain liposomal antiviral agent.

The compositions of antiviral agent according to the present disclosure could be formulated by addition of free form antiviral agent to target at a concentration of the antiviral agent at a concentration of from 1.0 mg/mL to 4 mg/mL, and the antiviral agent to the lipids at ratios of from at least 0.05 mol/mol to 0.30 mol/mol (See below Formulation #4 to #6) on the basis of the whole composition respectively.

| Formulation | #4 | #5 | #6 |
|---|---|---|---|
| HCQ (mg/ml) | 1.46 | 2.00 | 2.00 |
| HCQ (mM) | 3.36 | 4.61 | 4.61 |
| DPPC (mM) | 30.0 | 45.0 | 22.8 |
| Cholesterol, mM | 20 | 30 | 15.2 |
| Total lipid (mM) | 50.0 | 75.0 | 38.0 |
| D/L (by total lipid) | 0.067 | 0.061 | 0.121 |

C. Storage Stability of Liposomal Antiviral Agent

The stability of liposomal hydroxychloroquine or chloroquine as prepared in above Sections A and B stored at 4° C. could be monitored for at least two weeks or a designed time period. Hydroxychloroquine or chloroquine loaded into empty liposomes by active loading with ammonium sulfate or by passive loading to obtain the liposomal drug samples could be studied. After storage of the liposomal drug sample at 4° C. or suitable temperature for over two weeks or a designed time period, the drug potency, physicochemical properties of liposomes could be studied over time.

Example 2 Pre-Clinical Evaluation of Inhaled Liposomal Antiviral Agent in an Animal Model The toxicity of an exemplary composition of liposomal hydroxychloroquine (HCQ) as prepared in Example 1B (also denoted as TLC19) in animal was investigated. One preliminary proof of concept pharmacokinetics (PK) and tissue distribution study in Sprague-Dawley (SD) rats following single-dose intravenous (IV)/intratracheal (IT) administration of HCQ sulfate solution (Free HCQ) or IT administration of a pilot formulation of TLC19 (Study No. PK20021) was conducted. The study was designed to investigate the tissue distribution, mainly lung, and systemic exposure of HCQ.

A total of 52 rats were assigned into three treatment groups; each rat received a single dose of HCQ via IT administration or IV injection. Blood and organ/tissue samples, including lungs, were collected at pre-designated time points at 0.25, 1 (blood only), 4, 24 and 72 hours post-dose and were used for the determination of HCQ via liquid chromatography with tandem mass spectrometry. The study design is summarized in the following Table 1.

TABLE 1

A Summary of Study Design (Study No. PK20021)

| Group | Test Article | Route of admin. | Dose Level (HCQ sulfate) | Sampling Time Point (Hour) | No. of Animal |
|---|---|---|---|---|---|
| 1 | Free HCQ | IV injection | 0.590 mg/animal | Organ/tissue: 0.25, 4, 24 and 72 | 12 (3/time point) |
| 2 | Free HCQ | IT administration | 0.590 mg/animal | Blood: 0.25, 1,4, 24 and 72 | 20 (5/time point) |

TABLE 1-continued

| A Summary of Study Design (Study No. PK20021) | | | | | |
|---|---|---|---|---|---|
| Group | Test Article | Route of admin. | Dose Level (HCQ sulfate) | Sampling Time Point (Hour) | No. of Animal |
| 3 | TLC19 (pilot formulation) | | 0.284 mg/animal | | 20 (5/time point) |

Figure 2:
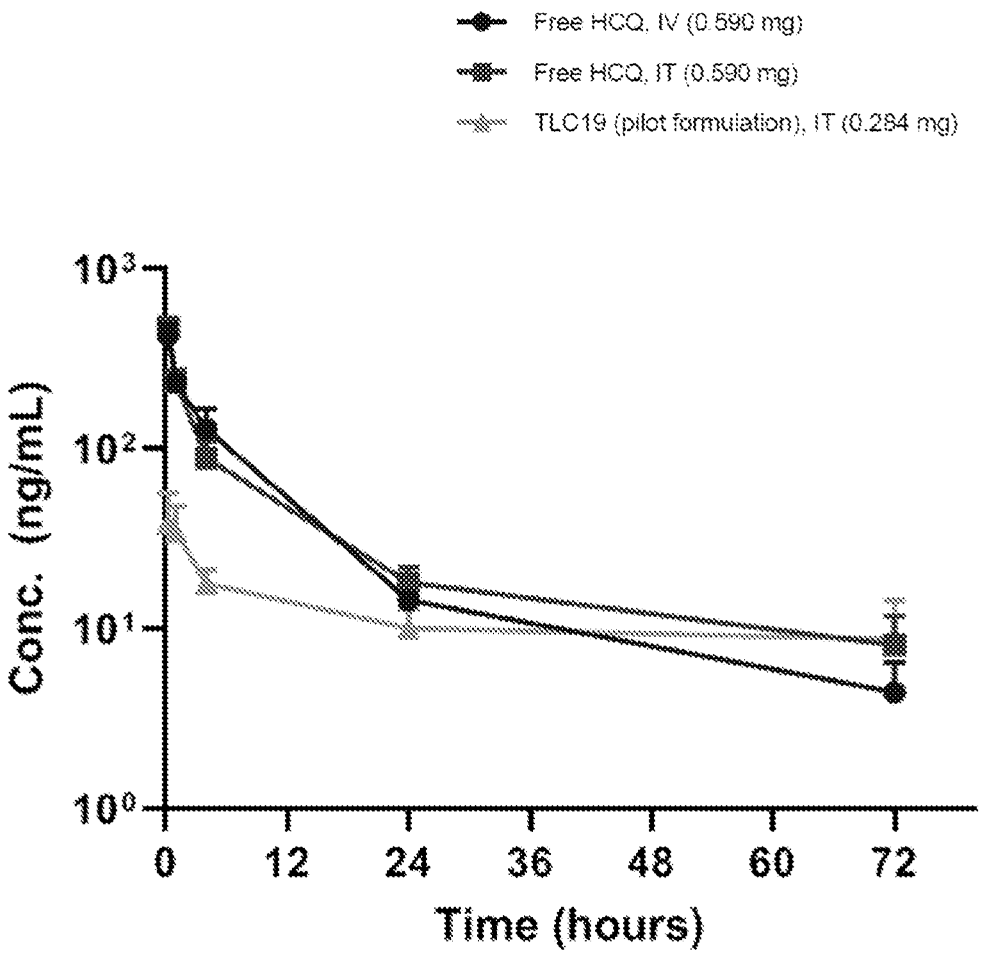
FIG. 2 depicting pharmacokinetic profiles of HCQ in rat blood following administration of the composition according to the present disclosure and free HCQ.
Figure 3:
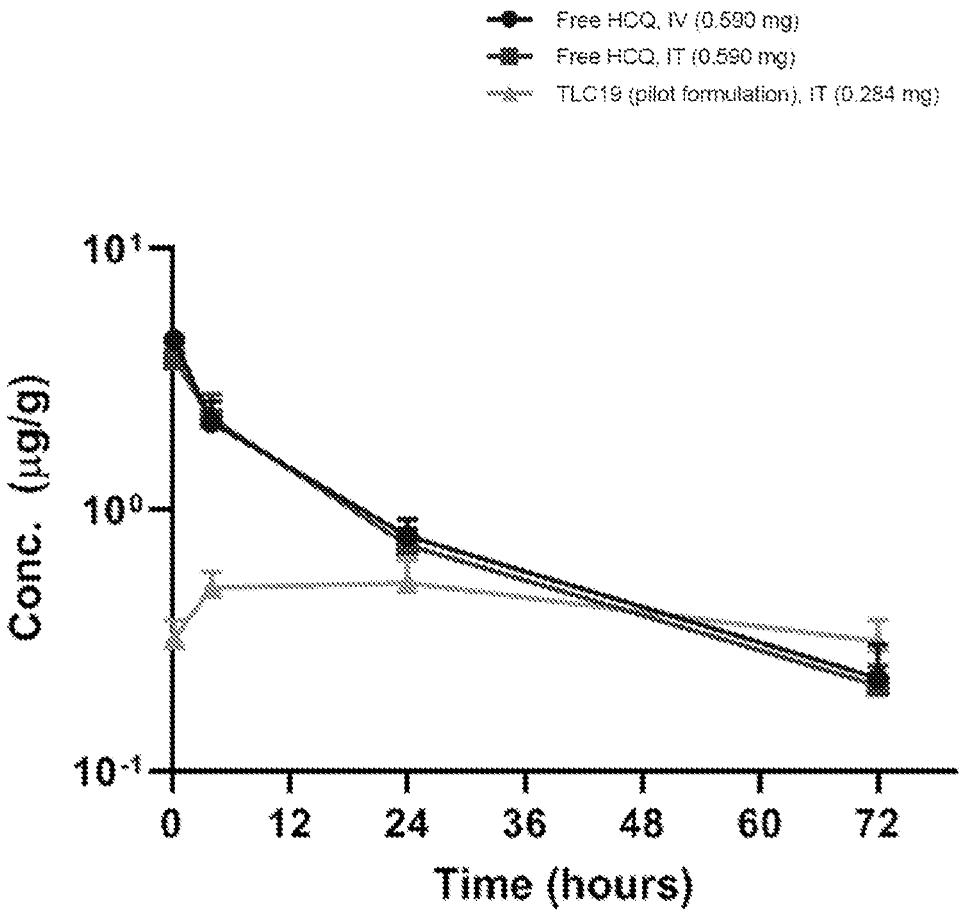
FIG. 3 depicting pharmacokinetic profiles of HCQ in rat heart following administration of the composition according to the present disclosure and free HCQ.

The concentrations of HCQ in blood, lung and heart were calculated by using Analyst® or MassLynx Software, while the pharmacokinetic PK parameters were determined using Phoenix® WinNonlin®. The HCQ concentration versus time profiles in lung, blood and heart following administration of TLC19 pilot formulation and Free HCQ are illustrated in FIG. 1, FIG. 2 and FIG. 3, respectively. Mean PK parameters of HCQ in lung, blood and heart are listed in Table 2.

TABLE 2

| Mean Pharmacokinetic Parameters of HCQ in Lung, Blood and Heart Following Administration of TLC19 and Free HCQ in Rat (Study No. PK20021) | | | | | | |
|---|---|---|---|---|---|---|
| Group | Dose (mg/animal) | Lung/ Blood | $T_{max}$[a] (Hour) | $C_{max}$ (μg/g or μg/mL)[b] | $AUC_{0-72}$ (hr*μg/g or hr*μg/mL)[c] | $T_{1/2}$ (Hour) |
| Free HCQ, IV | 0.590 | Lung | 0.25 | 9.4 | 252 | 15.2 |
| | | Blood | 0.25 | 0.433 | 2.33 | 15.3 |
| | | Heart | 0.25 | 4.5 | 67.2 | 21.8 |
| Free HCQ, IT | 0.590 | Lung | 0.25 | 47.8 | 329 | 17.7 |
| | | Blood | 0.25 | 0.477 | 2.26 | 22.1 |
| | | Heart | 0.25 | 3.8 | 64.2 | 21.0 |
| TLC19 (pilot formulation) | 0.284 | Lung | 0.25 | 129.4 | 4193 | 37.5 |
| | | Blood | 0.25 | 0.042 | 0.828 | 55.2 |
| | | Heart | 24 | 0.5 | 32.1 | NA[d] |

[a]$T_{max}$ presented as median.
[b]unit for lung and heart: μg/g; unit for blood: μg/mL
[c]unit for lung and heart: hr*μg/g; unit for blood: hr*μg/mL
[d]not applicable Regarding the lung distribution in rat administered with Free HCQ, the HCQ concentration declined constantly and rapidly, especially in the Free HCQ IT administration group, during the first 24 hours post-dose; the mean HCQ concentration declined from 47.8 μg/g to 2.16 μg/g in IT group and from 9.4 μg/g to 3.77 μg/g in IV group. In contrast, the extent of HCQ deposition in lung was elevated significantly for the TLC19 (pilot formulation) group compared to the Free HCQ group, which is attributed to the sustained-release characteristic of liposomal drug; the TLC19 group sustained release of HCQ in the lung for a certain period of time as the mean HCQ concentration declined from 129 μg/g to 57.1 μg/g during the first 24 hours post-dose after administration of half the Free HCQ dose.

The half-life of HCQ in lung in Free HCQ IV and IT groups were 15.2 hours and 17.7 hours, respectively, which is consistent with HCQ's physicochemical properties that HCQ could move freely across cell membranes rapidly at physiological pH. The half-life of HCQ in TLC19 (pilot formulation) group (37.5 hours) was about twice of the Free HCQ groups. The lung exposure with regards to $AUC_{0-72}$ and $C_{max}$ of TLC19 (pilot formulation) group were thirty-five and twenty-nine folds, respectively, of that of Free HCQ IV group when normalized with dose. These results suggest that TLC19 (pilot formulation), the sustained released formulation of HCQ, successfully extended lung residence time of HCQ compared to the Free HCQ via IV or IT administration. And in our study, neither IV nor IT administration of Free HCQ could maintain HCQ concentration in lung for a long time.

For systemic exposure, HCQ was absorbed and distributed to the system rapidly after HCQ administration. The median $T_{max}$ of HCQ in blood in three groups was at 0.25 hours after dosing. The overall systemic exposures, including $C_{max}$ and AUC, were similar in Free HCQ IV and IT groups. For TLC19 (pilot formulation), $C_{max}$ of HCQ in blood was significantly lower than that of Free HCQ. A small amount of HCQ resulted in an initial peak concentration within 1 hour after administration of TLC19 (pilot formulation). The remaining HCQ stayed in the lung, allowing for prolonged residence time and constantly low mean blood concentrations of TLC19 (pilot formulation) between 24 to 72 hours post-dose. The lower blood HCQ concentration levels observed over time suggest that the HCQ was gradually released at the local site. As reflected by its greater half-life, TLC19 (pilot formulation) demonstrated a longer release profile than the unformulated HCQ solution.

HCQ has been shown to cause cardiac disorder, including prolongation of the corrected QT interval (QTc). To determine the distribution of TLC19 in heart, the HCQ PK profile in heart tissue was determined (FIG. 3). TLC19 possessed lower heart exposure ($C_{max}$) when compared to HCQ solution. Similar AUCs were observed in all groups when dose is normalized. Considering the lower dose required for local (i.e. IT administration) rather than systemic administration (i.e. oral or IV), these results suggest that TLC19 could cause less cardiotoxicity than conventional HCQ administration.

Two pre-clinical PK studies will be conducted for TLC19 optimized formulation via IT administration in Sprague-Dawley (SD) rats and descript as follows.

(1) Single-dose PK study in SD rats: Blood pharmacokinetics and tissue concentration study following single-dose IT administration of TLC19 could be conducted in the SD rat. Blood and major organs, including lungs, could be collected at scheduled sampling time points; concentrations of HCQ will be determined for whole blood and organs. The preliminary PK profiles of TLC19 could be determined; the percentage of drug distribution of TLC19 in the lung could also be calculated.

(2) Multiple-dose PK study in SD rats: The study is designed to characterize and evaluate the drug accumulation of TLC19 following multiple-dose IT administrations. Blood and major organs, including lungs, could be collected at scheduled sampling time points after the first and the last doses. The accumulation rate of TLC19 in blood and lung could be calculated.

Example 3 Preparation of Liposomal Antiviral Agent

Sulfobutylether-β-cyclodextrin (SBECD) was purchased from Zibo Qianhui Biological Technology co., ltd, China. SBECD formulated GS-441524 (containing 1.0 mg/mL GS-441524) was prepared by dissolving GS-441524 (antiviral agent) in a 150 mg/mL SBECD solution with a pH of ~4.4 and was used as test article (1) GS-441524 Solution-IV.

The study drug (liposomal GS-441524, also denoted as ISPM21) was prepared by Taiwan Liposome Company, Ltd., Taiwan. It is composed of GS-441524 encapsulated in liposomes with mean particle size around 200 nm. GS-441524 was provided by *Formosa* Pharmaceuticals, Inc. as a pure, pale yellow powder. The liposomes are composed of dipalmitoylphosphatidylcholine (Nippon Fine Chemical co., ltd., Japan) and cholesterol (Dishman, The Netherlands), both of which are natural components of lung surfactant[23]. Empty, preformed liposome was prepared via solvent injection. Briefly, appropriate amounts of lipid mixture (1,2-dipalmitoyl-sn-glycero-3-phosphocholine (DPPC) and cholesterol) were dissolved in ethanol (J.T. Baker, USA) and injected into an ammonium sulfate solution while stirring at 50° C. Using an extruder, the size of the liposomes was adjusted to around 200 nm by extrusion through a 0.2 μm polycarbonate membrane at 50° C. Unencapsulated ammonium sulfate and ethanol were removed by diafiltration to obtain the final empty liposome.

Encapsulation of GS-441524 in liposome was performed using an active loading method. Empty, preformed liposome was mixed with GS-441524 drug solution and incubated at 50° C. to obtain the final ISPM21 sample (a liposomal drug suspension), which had a pH between 6 and 7, and was used as test article (2) ISPM21-IT.

A. Preparation of Liposomal Nucleoside Compound

I. Preparation of Empty Liposomes

Liposomes could be prepared via the thin-film hydration method or solvent injection method.

The process for preparing empty liposomes by solvent injection method is embodied by the method comprising the following steps:

1. weighing out lipid mixture of phospholipids, cholesterol at a predetermined molar ratio in the presence or absence of DSPE-PEG2000 and dissolving them by ethanol at elevated temperature;
2. preparing a trapping agent solution (e.g. ammonium sulfate (A.S.)) by adding a trapping agent to distilled water and mixing the solution to dissolve the salt;
3. adding the lipid mixture into the trapping agent solution at suitable temperature depending on the lipid composition to form a liposome solution;
4. extruding obtained liposome solution through polycarbonate membrane at suitable temperature depending on the lipid composition to get the designed particle size;
5. diafiltration of the extruded liposome against sucrose solution or saline or suitable buffer to remove free trapping agent and ethanol.

II. Drug Loading of an Antiviral Agent into Liposome

The following method represents a typical protocol for the encapsulation of nucleoside compound in liposome by remote loading, which comprises steps of:

1. preparing a solution of 15.4 mg/mL or suitable concentration of nucleoside compound in a suitable medium to obtain a stock solution containing nucleoside compound (hereafter denoted as stock solution);
2. mixing together empty liposomes as prepared by the process according to Example 1, section (A), section (I) [in a typical embodiment, with the condition of: DPPC:cholesterol at a molar ratio of 3:2, 300 mM ammonium sulfate (A.S.) as trapping agent, and 20-50 mM phospholipid concentration], and the stock solution into a conical tube to obtain a loading solution, targeting a D/L ratio to be 25 g/mol or a designed D/L ratio;
3. continuously shaking the loading solution at suitable temperature for 60 minutes or a designed time period to form the drug loaded liposomes;
4. adding NaOH solution or buffer solution to the drug loaded liposomes to adjust the pH of solution to between 6.0 to 7.0; and
5. determining the drug encapsulation (i.e. loading efficiency) of the final sample using size-exclusion column chromatography and UV-Vis absorbance measurements or HPLC analysis.

TABLE A

The drug loading profile of different drug to lipid ratio

| Formulation of liposome | GS-441524 (mM) | Total lipid (mM) | D/L (mol/mol) | Encapsulation efficiency |
|---|---|---|---|---|
| DPPC:cholesterol = 3:2 (trapping 300 mM A.S.) | 13.7 | 41.7 | 0.330 | 45.1% |
| | 3.4 | 41.7 | 0.082 | 73.1% |
| | 3.4 | 58.3 | 0.059 | 89.3% |
| | 3.4 | 66.7 | 0.052 | 95.5% |
| | 3.4 | 83.3 | 0.041 | 96.0% |

*The encapsulation efficiency (EE) is calculated by the formula: the liposomal form (LF) of the drug divided by the total form (TF) of the drug: EE(%) = LF/TF*100%.

B. Storage Stability of Liposomal Antiviral Agent

The stability of liposomal nucleoside compound stored at 4° C. could be monitored for at least two months or a designed time period. Nucleoside compound loaded into empty liposomes with 300 mM of ammonium sulfate or 75 mM of triethylammonium sucrose octasulfate as trapping agent to obtain the liposomal drug samples (Table A) could be studied. After storage of the liposomal drug sample at 4° C. or suitable temperature for over two months or a designed time period, the drug potency, physicochemical properties of liposomes could be studied over time.

Example 4 Releasing Profile of the Liposomal Antiviral Agent

In Vitro Drug Release in Simulated Lung Fluid

The release profile experiments of liposomal antiviral agent prepared by Example 1 could be performed to demonstrate their sustained release properties. The protocol for the in vitro release (IVR) experiments is outlined as follows:

1. diluting the test article 10-fold by mixing 0.5 mL of each sample of the liposomal antiviral agent with 4.5 mL of SLF (pre-warmed at 37° C.) and placing the diluted sample in a 15-mL centrifuge tube;
2. placing the centrifuge tubes containing the diluted samples onto sample wells of a Intelli-mixer rotator and rotating at 20 rpm, incubating at 37° C.; and
3. sampling 1 mL of the diluted samples at predetermined time points for analyzing encapsulated efficiency.

The analytical method for determining the nucleoside compound encapsulation efficiency is as follows:

a. packing and washing 2 mL of a G50 column with condition solution;
b. adding 0.1 mL of the sample to the column, then adding 0.45 mL of an eluent and waiting for the solution to be eluted out;
c. adding 0.8 mL of eluent to the column and collecting the eluate as liposomal form;
d. disrupting the pre- and post-column samples (the liposome form and the total form) by suitable solvent; and
e. measuring the absorbance of the samples at the indicated wavelength using a UV-Vis or HPLC method to determine the drug concentrations of each sample.

The encapsulation efficiency (EE) of the antiviral agent in the liposomes could be calculated and obtained by the formula: the liposomal form (LF) of the drug divided by the total form (TF) of the drug:

$$EE(\%)=LF/TF*100\%.$$

The releasing profile could be plotted to depict the releasing rate (%) versus time. The releasing rate could be calculated by the formula: the initial liposomal form minus liposomal form at each time point and then divide by the initial liposomal form:

$$(LF_{t0}-LF_{t})/LF_{t0}*100\%.$$

A prolonged release profile of drug substance is desired for improved efficacy and treatment of with lower dosing frequency. Therefore, the selected liposomal antiviral agent with slower or suitable releasing profiles among all formulations and used them in the following toxicity study.

Example 5 Pharmacokinetics of Inhaled Liposomal Antiviral Agent in an Animal Model Study Design A total of 48 female SD rats (BioLASCO Taiwan Co., Ltd.) were assigned to one of two treatment groups: (1) GS-441524 Solution-IV: 24 rats received a single dose of 0.20 mg GS-441524 per animal via IV injection; (2) ISPM21-IT: 24 rats received a single dose of 0.20 mg ISPM21 (liposome suspension containing 1.0 mg/mL GS-441524) per animal via IT instillation, which is an administration route used to mimic inhalation in a clinical setting. The sampling time points for blood samples were 0.25, 1, 4, 24, and 72 hours post-dose and for lung samples were 0.25, 4, 24, and 72 hours post-dose. All procedures involving animals were performed in TLC animal facility and in accordance with the ethical guidelines of Institutional Animal Care and Use Committee (IACUC) at TLC, Taiwan (#TLC20IACUC037).

Blood and Lung Sample Collection and Handling

Blood was collected from jugular veins at scheduled sampling time points into collection tubes with $K_2EDTA$ as the anticoagulant. Each collection tube was gently inverted to ensure that samples were completely mixed with the anticoagulant. The actual sampling time was recorded. Collected blood samples were centrifuged at 1,500×g for 10 minutes at 2-8° C. to obtain plasma. Supernatant plasma was immediately transferred into a labelled microtube. Plasma was transferred to a freezer set at −80° C., if not processed immediately. Plasma harvesting was completed within two hours following blood collection.

Animals were euthanized at scheduled lung sample collection times. Each rat was perfused with about 100 mL of 2 mM $K_2EDTA$/saline solution for at least 8 minutes by KD Scientific® Syringe Pump. After perfusion, lungs were taken and frozen in liquid nitrogen. After freezing, lungs were weighed and placed on wet ice until transferred to a −80° C. freezer. All lung samples were stored in a −80° C. freezer until homogenization.

Bioanalysis and PK Calculation

Blood Samples were Added with Internal Standard (6,7-Dimethyl-2,3-di-2-pyridylquinoxaline) before mixing well with methanol for protein precipitation. After centrifugation, the supernatant was injected into a liquid chromatography (Waters I-Class UPLC) coupled with tandem mass spectrometer (Waters Xevo™ TQ-S) (LC-MS/MS) for analysis. For lung samples, tissue/organ was homogenized with 50% methanol with 0.1% formic acid. The tissue/organ homogenate was added with internal standard (IS) before mixing well with methanol for protein precipitation. The resulting sample supernatant was injected into LC-MS/MS for analysis after centrifugation. Concentrations of GS-441524 were calculated using MassLynx software. The linear ranges were 10-10000 ng/mL and 0.5-500 ng/mL for lung and plasma assay, respectively. PK parameters of GS-441524 were calculated by non-compartmental method applying sparse sampling computation using Phoenix® WinNonlin® (version 8.0 or above).

Results

GS-441524 Pharmacokinetics in Lung

Figure 4A:
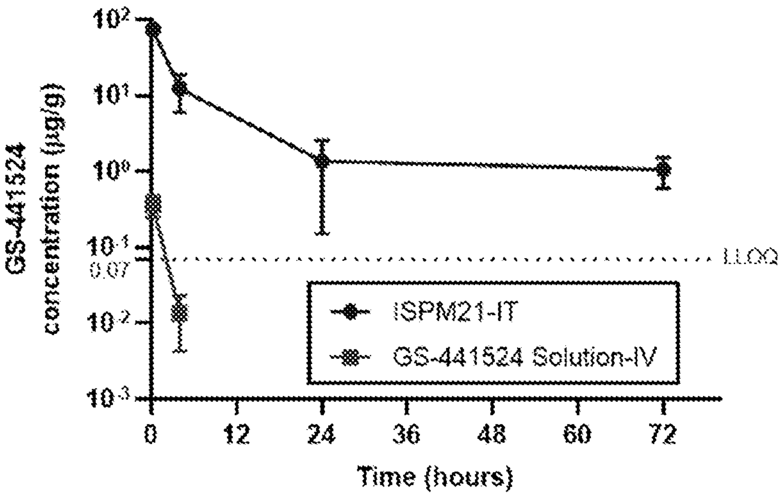
FIGS. 4A and 4B showing a series of graphs depicting mean concentration-time profiles of GS-441524 in rat lung (FIG. 4A) and plasma (FIG. 4B) after a single IV administration of SBECD formulated GS-441524 (GS-441524 Solution-IV) or a single IT administration of liposomal GS-441524, also denoted as ISPM21 (ISPM21-IT); LLOQ: lower limit of quantification.

After a single dose IT administration of ISPM21, a long half-life (22.8 hours) and higher GS-441524 levels (FIG. 4A) in lung were observed for ISPM21-IT compared to GS-441524 Solution-IV (Table 3). The half-life and AUC of GS-441524 Solution-IV in lung could not be calculated due to the concentration only being measurable at the first time-point (0.25 hours). Notably, a single dose of 0.2 mg ISPM21-IT achieved $C_{max}$ of 74.9 μg/g and $AUC_{0-72}$ of 369 hμg/g, showing drastically higher lung exposure with 207-fold in $C_{max}$ compared to GS-441524 Solution-IV (Table 4).

TABLE 3

Pharmacokinetic parameters of GS-441524 in rat lung and plasma after a single administration of GS-441524 Solution-IV or ISPM21-IT

| | Lung | | Plasma | |
|---|---|---|---|---|
| PK parameters | GS-441524 Solution-IV | ISPM21-IT | GS-441524 Solution-IV | ISPM21-IT |
| $T_{max}$ (h)[a] | 0.25 | 0.25 | 0.25 | 1 |
| $C_{max}$ (μg/g or ng/mL)[b] | 0.36 | 74.9 | 470 | 172 |

TABLE 3-continued

Pharmacokinetic parameters of GS-441524 in rat lung and plasma after a single administration of GS-441524 Solution-IV or ISPM21-IT

| | Lung | | Plasma | |
|---|---|---|---|---|
| PK parameters | GS-441524 Solution-IV | ISPM21-IT | GS-441524 Solution-IV | ISPM21-IT |
| $AUC_{0-t}$ (h*μg/g or h*ng/mL)[c] | N/A | 369 | 916[d] | 1,010[d] |
| $AUC_{\infty}$ (h*μg/g or h*ng/mL)[c] | N/A | 404 | 918[d] | 1,013[d] |
| $t_{1/2}$ (h) | N/A | 22.8 | 7.43[d] | 9.98[d] |

[a]$T_{max}$ was presented as median for plasma

[b]$C_{max}$ unit: μg/g for lung; ng/mL for plasma

[c]Unit: h*μg/g for lung; h*ng/mL for plasma

[d]The calculation included the extrapolated value at 72 hours time-point

TABLE 4

Ratios of dose-normalized maximum concentration and area under the concentration-time curve for ISPM21-IT to GS-441524 Solution-IV ISPM21-IT to GS-441524 Solution-IV

| Specimen | $C_{max}$ ratio | $AUC_{0-t}$ ratio |
|---|---|---|
| Lung | 207 | N/A |
| Plasma | 0.37 | 1.10 |

GS-441524 Pharmacokinetics in Plasma

Figure 4B:
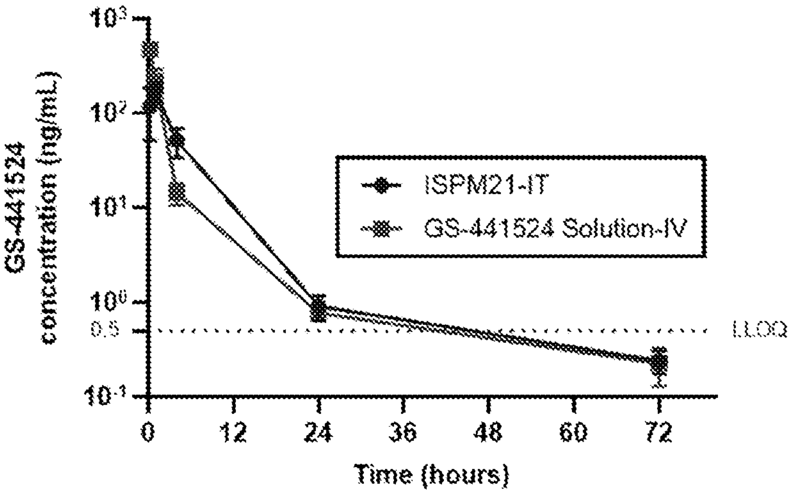

After a single dose administration, ISPM21-IT showed similar PK profile (FIG. 4B) and AUC (Tables 3 and 4) in plasma compared to GS-441524 Solution-IV. The plasma half-life of ISPM21-IT (9.98 hours) was slightly longer than that of GS-441524 Solution-IV (7.43 hours). Notably, ISPM21-IT showed lower systemic exposure (37% of $C_{max}$) in plasma compared to GS-441524 Solution-IV (Table 4).

In this rat PK study, targeted delivery of inhalable ISPM21 to the lung was investigated and sustained release with significantly higher exposure of GS-441524 in lung was demonstrated. After single IT administration of ISPM21, the mean concentration of GS-441524 in lung after 72 hours post-dose was 1.07 μg/g (3.67 μM, assuming the density of lung tissue sample is 1 g/mL), indicating ISPM21 could maintain a relatively high GS-441524 concentration, which is 19-fold higher than the in vitro antiviral $EC_{50}$ of 0.18 μM against SARS-CoV-infected human airway epithelial (HAE) cells in the lung.

What is claimed is:

1. A composition of antiviral agent for use in prophylaxis or treatment of a respiratory disease or an infectious disease via inhalation, which comprises liposomal antiviral agent, wherein the liposomal antiviral agent comprises:

a liposome comprising one or more phospholipids and a sterol, and the molar ratio of the total phospholipids to the sterol ranges from 1:1 to 2:1, and an antiviral agent encapsulated in the liposome;

wherein the composition has a ratio of the antiviral agent to the total lipid ranging from 0.01 mol/mol to 2.0 mol/mol; and wherein the antiviral agent is a nucleoside compound of structural formula (I):

(I)

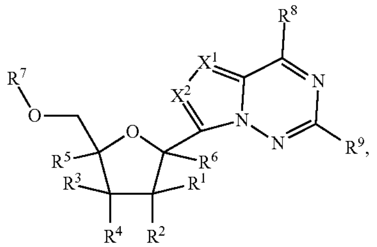

each $R^1$, $R^2$, $R^3$, $R^4$ or $R^5$ is independently H, $OR^a$, $N(R^a)_2$, $N_3$, CN, $NO_2$, $S(O)_nR^a$, halogen or methyl, wherein n is 0, 1 or 2;

$R^6$ is CN or H;

each $R^a$ is independently H, $(C_1\text{-}C_8)$alkyl, $(C_2\text{-}C_8)$alkenyl, $(C_2\text{-}C_8)$alkynyl, aryl$(C_1\text{-}C_8)$alkyl, $(C_4\text{-}C_8)$carbocyclylalkyl, $—C(═O)R^{11}$, $—C(═O)NR^{11}$, $—C(═O)NR^{11}R^{12}$, $—C(═O)SR^{11}$, $—S(O)R^{11}$, $—S(O)_2R^{11}$, $—S(O)_2(OR^{11})$, $—S(O)_2(OR^{11})$, or $—SO_2NR^{11}R^{12}$; and $R^7$ is H;

Each $X^1$ or $X^2$ is independently $C\text{-}R^{10}$ or N;

$R^8$ is halogen, $NR^{11}R^{12}$, $N(R^{11})(OR^{11})$, $N R^{11}NR^{11}R^{12}$, $N_3$, NO, $NO_2$, CHO, CN, $—CH(═NR^{11})$, $—CH═NHNR^{11}$, $—CH═N(OR^{11})$, $—CH(OR^{11})_2$, $—C(═O)NR^{11}R^{12}$, $—C(═S)NR^{11}R^{12}$, $—C(═O)OR^{11}$, $(C_1\text{-}C_8)$alkyl, $(C_2\text{-}C_8)$alkenyl, $(C_2\text{-}C_8)$alkynyl, aryl$(C_1\text{-}C_8)$ alkyl, $(C_4\text{-}C_8)$carbocyclylalkyl, optionally substituted aryl, optionally substituted heteroaryl, $—C(═O)(C_1\text{-}C_8)$alkyl, $—S(O)_n(C_1\text{-}C_8)$alkyl, aryl$(C_1\text{-}C_8)$alkyl, $OR^{11}$ or $SR^{11}$; wherein each aryl or heteroaryl is independently optionally substituted with one or more Z groups;

each $R^9$ or $R^{10}$ is independently H, halogen, $R^{11}$, $OR^{11}$, $SR^{11}$, $NR^{11}R^{12}$, $N(R^{11})(OR^{11})$, $N R^{11}NR^{11}R^{12}$, $N_3$, NO, $NO_2$, CHO, CN, $—CH(═NR^{11})$, $—CH═NHNR^{11}$, $—CH═N (OR^{11})$, $—CH(OR^{11})_2$, $—C(═O)NR^{11}R^{12}$, $—C(═S)NR^{11}R^{12}$, $—C(═O)OR^{11}$;

each $R^{11}$ or $R^{12}$ is independently H, $(C_1\text{-}C_8)$alkyl, $(C_2\text{-}C_8)$alkenyl, $(C_2\text{-}C_8)$alkynyl, $(C_4\text{-}C_8)$carbocyclylalkyl, optionally substituted aryl, optionally substituted heteroaryl, $—C(═O)(C_1\text{-}C_8)$alkyl, $—S(O)_n(C_1\text{-}C_8)$alkyl or aryl$(C_1\text{-}C_8)$alkyl; wherein each aryl or heteroaryl is independently optionally substituted with one or more Z groups;

or $R^{11}$ or $R^{12}$ taken together with a nitrogen to which they are both attached form a 3 to 7 membered heterocyclic ring wherein any one carbon atom of said heterocyclic ring can optionally be replaced with —O—, —S— or $—NR^a—$, each Z group is independently halogen, $—O^-$, ═O, $—OR^b$, $—SR^b$, —S—, $—NR^b_2$, $—N^+R^b_3$, $═NR^b$, —CN, —OCN, —SCN, —N═C═O, —NCS, —NO, $—NO_2$, $═N_2$, $—N_3$, $—NHC(═O)R^b$, $—OC(═O)R^b$, $—NHC(═O)NR^b2$, $—S(═O)_2—$, $—S(═O)_2OH$, $—S(═O)_2R^b$, $—OS(═O)_2Or^b$, $—S(═O)_2OH$, $—S(═O)R^b$, $—OP(═O)(OR^b)_2$, $—P(═O)(OR^b)_2$, $—P(═O)(O—)_2$, $—P(O)(OR^b)(O—)$, $—C(═O)R^b$, $—C(═O)X$, $—C(S)R^b$, $—C(O)OR^b$, —C(O)O—, $—C(S)OR^b$, $—C(O)SR^b$, $—C(S)SR^b$, $C(O)NR^b_2$, —C(S)$NR^b_2$, —C(═$NR^b$)$NR^b_2$, where in each $R^b$ is independently H, alkyl, aryl, arylalkyl or heterocycle; wherein one or more of the non-terminal carbon atoms of each said ($C_1$-$C_8$) alkyl is optionally replaced with —O—, —S— or —$NR^a$—.

2. The composition of antiviral agent for use according to claim 1, wherein the sterol is cholesterol.

3. The composition of antiviral agent for use according to claim 1, wherein the one or more phospholipid is selected from the group consisting of hydrogenated soy phosphatidylcholine (HSPC), 1,2-distearoyl-sn-glycero-3-phosphocholine (DSPC), 1,2-dipalmitoyl-sn-glycero-3-phosphocholine (DPPC), phosphatidylethanolamine lipid, 1,2-dipalmitoyl-sn-glycero-3-phosphoethanolamine (DPPE), and combinations thereof.

4. The composition of antiviral agent for use according to claim 1, wherein the liposomal antiviral agent has a mean particle diameter at a range between 50 nm and 1,000 nm.

5. The composition of antiviral agent for use according to claim 1, which further comprises an antibiotic.

6. The composition of antiviral agent for use according to claim 5, wherein the antibiotic is selected from the group consisting of currimycin and azithromycin.

7. The composition of antiviral agent for use according to claim 1, which has a total lipid concentration at a range from 1 mM to 100 mM.

8. The composition of antiviral agent for use according to claim 1, which further has a free form antiviral agent.

9. The composition of antiviral agent for use according to claim 1, wherein the ratio of the antiviral agent to the total lipid ranges from 0.05 mol/mol to 2.0 mol/mol.

10. The composition of antiviral agent for use according to claim 1, wherein the antiviral agent has a concentration ranging from about 0.1 mg/mL to about 80 mg/mL.

11. The composition of antiviral agent for use according claim 1, wherein the composition is a nebulized spray.

12. An aerosolized composition of particles, which comprises the composition of antiviral agent according to claim 1 wherein the aerosolized composition of particles is for use in prophylaxis or treatment of an infectious disease or a respiratory disease via inhalation.

13. The aerosolized composition of particles according to claim 12, wherein the multiple particles have a mass median aerodynamic diameter ranging from about 0.5 μm to 5 μm.

14. The composition of antiviral agent for use according to claim 1, wherein the antiviral agent is encapsulated in the liposome by remote loading using a trapping agent, wherein the trapping agent is composed of an ammonium compound and an anionic counterion, and wherein the anionic counterion is selected from the group consisting of sucrose octasulfate, dextran sulfate, sulfate, citrate, gluconate, sulfonate, phosphate, pyrophosphate, tartrate, succinate, maleate, borate, carboxylate, bicarbonate, glucuronate, chloride, hydroxide, nitrate, cyanate, bromide and combinations thereof.

15. The composition of antiviral agent for use according to claim 1, wherein the liposome further comprises a polyethylene glycol (PEG)-modified lipid at an amount ranging from 0.0001 mol % to 10 mol %, optionally less than 6 mol %, optionally ranges from 0.001 mol % to 5 mol % on the basis of the total lipids.

16. The composition of antiviral agent for use according to claim 15, wherein the PEG-modified lipid has a PEG moiety with an average molecular weight ranging from 1,000 g/mol to 5,000 g/mol.

17. The composition of antiviral agent for use according to claim 15, wherein the PEG-modified lipid is 1,2-distearoyl-sn-glycero-3-phosphoethanolamine-N-[methoxy (polyethylene glycol)] (DSPE-PEG).

18. The composition of antiviral agent for use according to claim 17, wherein the amount of DSPE-PEG of the liposome ranges from 0.001 to 5 mol % on the basis of the total phospholipid and sterol.

19. The composition of antiviral agent for use according to claim 1, wherein the antiviral agent is selected from the group consisting of:

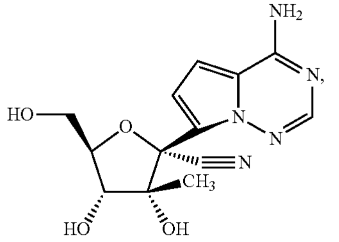

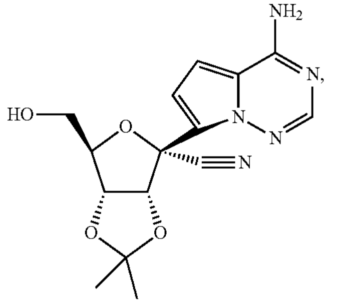

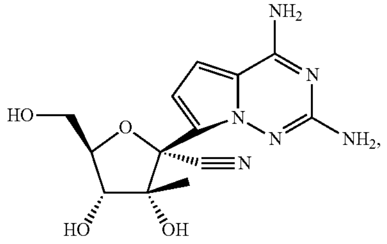

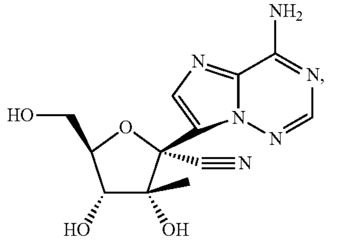

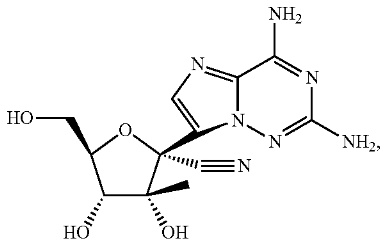

-continued

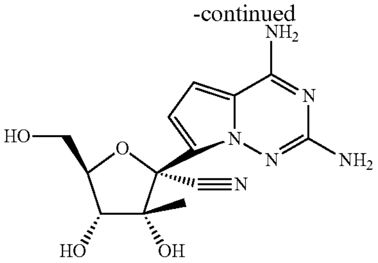

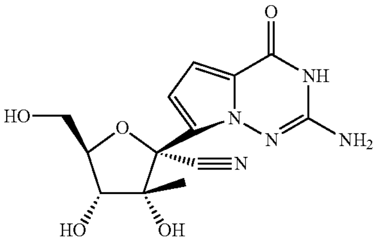

or a pharmaceutically acceptable salt thereof.

20. The composition of antiviral agent for use according to claim 10, which has a concentration of the antiviral agent ranging from 0.5 to 5 mg/mL.

21. A method for treating infectious or respiratory disease, which comprises:

administering the pharmaceutical composition of antiviral agent for use according to claims 1, 2-4, 5-10, 11, 14-18, 19 or 20 to a subject in need thereof.

22. The method according to claim 21, wherein the respiratory disease is selected from the group consisting of: severe acute respiratory infection (SARI), including severe pneumonia, acute respiratory distress syndrome (ARDS), sepsis and septic shock.

23. The method according to claim 21, wherein the infectious disease is caused by virus, optionally influenza virus or retrovirus, optionally coronavirus, and optionally SARS-CoV-2.

* * * * *